United States Patent
Port

(10) Patent No.: US 9,895,100 B2
(45) Date of Patent: Feb. 20, 2018

(54) EYE MOVEMENT MONITORING OF BRAIN FUNCTION

(71) Applicant: Indiana University Research and Technology Corporation, Indianapolis, IN (US)

(72) Inventor: Nicholas L. Port, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/026,229

(22) PCT Filed: Oct. 3, 2014

(86) PCT No.: PCT/US2014/059098
§ 371 (c)(1),
(2) Date: Mar. 30, 2016

(87) PCT Pub. No.: WO2015/051272
PCT Pub. Date: Apr. 9, 2015

(65) Prior Publication Data
US 2016/0213301 A1 Jul. 28, 2016

Related U.S. Application Data

(60) Provisional application No. 61/886,982, filed on Oct. 4, 2013.

(51) Int. Cl.
*A61B 6/00* (2006.01)
*A61B 5/00* (2006.01)
(Continued)

(52) U.S. Cl.
CPC ............ *A61B 5/4064* (2013.01); *A61B 3/113* (2013.01); *A61B 5/11* (2013.01); *A61B 5/4076* (2013.01);
(Continued)

(58) Field of Classification Search
CPC .......... A61B 3/00; A61B 3/0008; A61B 3/02; A61B 3/022; A61B 3/024; A61B 3/028;
(Continued)

(56) References Cited

U.S. PATENT DOCUMENTS

| 4,838,681 A | 6/1989 | Pavlidis |
| 6,090,051 A | 7/2000 | Marshall |

(Continued)

FOREIGN PATENT DOCUMENTS

WO WO2013148557 A1 10/2013

OTHER PUBLICATIONS

International Search Report and Written Opinion issued by the ISA/US Commissioner for Patents, dated Jan. 14, 2015, for International Application No. PCT/US2014/059098; 9 pages.

(Continued)

*Primary Examiner* — Christopher D Koharski
*Assistant Examiner* — Elizabeth K So
(74) *Attorney, Agent, or Firm* — Faegre Baker Daniels LLP

(57) ABSTRACT

The present disclosure provides a wearable device for the detection of mild traumatic brain injury, such as concussions, and methods of use thereof. Further disclosed are a method and system for detecting a mild traumatic brain injury.

31 Claims, 14 Drawing Sheets

(51) Int. Cl.
*A61B 3/113* (2006.01)
*A61B 5/11* (2006.01)

(52) U.S. Cl.
CPC .......... *A61B 5/6814* (2013.01); *A61B 5/7246* (2013.01); *A61B 5/7282* (2013.01); *A61B 5/743* (2013.01); *A61B 5/4082* (2013.01); *A61B 5/4842* (2013.01); *A61B 5/4863* (2013.01); *A61B 5/7405* (2013.01); *A61B 2503/10* (2013.01)

(58) Field of Classification Search
CPC ..... A61B 3/0285; A61B 3/032; A61B 3/0325; A61B 3/036; A61B 3/06; A61B 3/063; A61B 3/066; A61B 3/113; A61B 5/00; A61B 5/4064; A61B 5/4082; A61B 5/4088; A61B 5/4094
See application file for complete search history.

(56) References Cited

U.S. PATENT DOCUMENTS

| | | |
|---|---|---|
| 8,048,002 B2 | 11/2011 | Ghajar |
| 8,668,337 B2 | 3/2014 | Waldorf et al. |
| 2004/0252277 A1 | 12/2004 | Chmielewski |
| 2006/0270945 A1 | 11/2006 | Ghajar |
| 2010/0094161 A1 | 4/2010 | Kiderman et al. |
| 2010/0208205 A1 | 8/2010 | Tseng et al. |
| 2011/0152711 A1 | 6/2011 | Della Santina et al. |
| 2012/0230547 A1 | 9/2012 | Durnell et al. |

OTHER PUBLICATIONS

Extended European Search Report issued by the European Patent Office, dated Apr. 10, 2017, for European Patent Application No. 14851258.5; 7 pages.

EYE MOVEMENT MONITORING OF BRAIN FUNCTION

PRIORITY CLAIM

This Application is a U.S. national stage filing of PCT/US2014/059098, filed on Oct. 3, 2014, which claims priority to U.S. Provisional Patent Application No. 61/886,982, filed Oct. 4, 2013, the entire disclosures of which are both hereby expressly incorporated herein by reference.

GOVERNMENT SUPPORT CLAUSE

This invention was made with government support under DC013974 and EY019008, awarded by the National Institutes of Health. The Government has certain rights in the invention.

FIELD

The present disclosure relates generally to a device for detecting when a person has suffered a mild traumatic brain injury (mTBI), such as a concussion. More particularly, the present disclosure relates to a portable, high-speed and high-resolution eye movement instrument capable of measuring eye movements, for example, on the side lines of an athletic field in full daylight conditions to detect an mTBI.

BACKGROUND AND SUMMARY

Over 1.5 million sport-related concussions or mild traumatic brain injuries occur annually in the United States. Increased media and medical attention is focused on these injuries and their potential to cause long-term cognitive, somatic, and affective problems. While detection of the low-level diffuse damage incurred through mTBI needs to take place accurately and quickly, assessment methods have been criticized as insufficiently sensitive and susceptible to motivational and other extraneous factors. Recent research shows that oculomotor performance (e.g., eye movements such as saccades and smooth pursuit) may represent a sensitive biomarker of mTBI.

The present disclosure provides a portable tool for the diagnosis and management of mTBI such as concussions. Such a tool for the detection of concussions is substantially completely automated, and therefore is not influenced by the will of an athlete, a coach, a parent, the media, or a sports fan. The same tool has other uses outside of sports for people with potential mTBIs, for example, in the military.

One exemplary embodiment of a field mTBI assessment tool: (a) evaluates an aspect of brain function that involves a broad range of structures, for example subcortical, cortical, and cerebellar so that diffuse, low level damage has a higher likelihood of detection; (b) is used to conduct a test rapidly following injury; (c) requires minimal time and cost; (d) is portable to sites of injury and recuperation; and (e) provides an assessment that is difficult for the test subject to manipulate in an attempt, for example, to conceal the existence of a concussion.

Thus, herein disclosed is a device to detect mild traumatic brain injury ("mTBI") by user eye movement which includes a visualization unit comprising a light and a camera, wherein the visualization unit is configured to reflect light off of a user's eye into the camera, a user screen viewable by the user and configured to display a series of tasks to the user, the tasks including at least saccade tasks and pursuit tasks, which require movement of the user's eye, such movements being tracked by the visualization unit, and a first computing device in communication with the visualization unit, wherein the first computing device receives eye movement data from the visualization unit in response to the user performing the series of tasks, the first computing device being configured to calculate a difference between at least one measured variable of the eye movement data when the user is unimpaired and the at least one measured variable after the user experiences a potential mTBI.

In some embodiments, the device is portable and wearable by the user. In other embodiments, the tasks further include at least one of a self-paced saccade task, a sinusoidal pursuit task, a step-ramp pursuit task, an ocular following task, and a dynamic random dot task. In some embodiments, the series of tasks requires between about three and about ten minutes to complete. In other embodiments, the series of tasks requires between about five and about eight minutes to complete. Still in other embodiments, a device configured to measure the user's balance during the series of tasks is included. Still in other embodiments, the device further comprises a second computing device and an operator's screen for operation of the visualization unit. In some embodiments, the device further comprises user controls and an audio unit.

In some other embodiments, the user's unimpaired baseline score for the at least one variable is an average of two baseline task scores for the user taken at two different times when the user is unimpaired. In some embodiments, the user screen and operator screen provide either an indication of likely concussed or likely not concussed based on the difference between the values of at least one measured variable.

Further disclosed is a method of detecting mild traumatic brain injury ("mTBI") comprising the steps of providing a visualization unit for a user suspected of suffering an mTBI which can track the user's eye movement and record resulting eye movement data by a camera and a first computing device, presenting to the user a series of tasks designed to require the user to move the user's eyes pursuant to specified directions, recording the user's eye movement data in response to the user performing the series of tasks, comparing the user's eye movement data to standard eye movement data for a person not suffering from mTBI, and determining whether the user has suffered an mTBI by analyzing a difference between the user's recorded eye movement data and the eye movement data for a person not suffering from mTBI.

In some embodiments, the visualization unit is portable and wearable by the user. In other embodiments, the tasks further include at least one of a self-paced saccade task, a sinusoidal pursuit task, a step-ramp pursuit task, an ocular following task, and a dynamic random dot task. Still in other embodiments, the method further comprises the step of providing a device configured to measure the user's balance during the series of tasks. In other embodiments, the step of executing further comprises a second computing device and an operator's screen for operation of the visualization unit. Still in other embodiments the visualization unit further comprises user controls and an audio unit.

Some embodiments further include the step of providing a visualization unit for a user not suspected of suffering an mTBI which can track and record the user's eye movement data by a camera and a first computing device, wherein the user's eye movement data provides the user's unimpaired baseline score for the at least one variable. Still other embodiments include providing an indication of likely concussed or likely not concussed based on the difference between the user's recorded eye movement data and the eye movement data for a person not suffering from mTBI.

Additionally disclosed is a system to detect mild traumatic brain injury ("mTBI") by user eye movement comprising a visualization unit comprising a light and a camera, wherein the visualization unit is configured to reflect light off of a user's eye into the camera, a user screen, wherein the screen is viewable by the user and wherein the screen is configured to display a series of tasks to the user to measure the user's eye movement by the camera, a device for measuring the user's balance during the series of tasks, a first computing device in communication with the visualization unit, wherein the first computing device receives eye movement data from the visualization unit in response to the user performing the series of tasks, the first computing device being configured to calculate a difference between at least one measured variable of the eye movement data when the user is unimpaired and the at least one measured variable after the user experiences a potential mTBI, and software-implemented logic to determine if the difference between the at least one measured variable of the user's eye movement between the user's unimpaired baseline score and the user's mTBI score is great enough to indicate a likelihood of an mTBI.

In some embodiments, the tasks further include at least one of a self-paced saccade task, a sinusoidal pursuit task, a step-ramp pursuit task, an ocular following task, and a dynamic random dot task. Still other embodiments further comprise a second computing device and an operator's screen for operation of the visualization unit. In some embodiments, the visualization unit further comprises user controls and an audio unit. In other embodiments, the user's unimpaired baseline score for the at least one variable is an average of two baseline task scores for the user taken at time when the user is unimpaired. Still in other embodiments, the user screen and operator screen provide either an indication of likely concussed or likely not concussed based on the difference between the values of the at least one measured variable.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawings.

DETAILED DESCRIPTION

Figure 1:
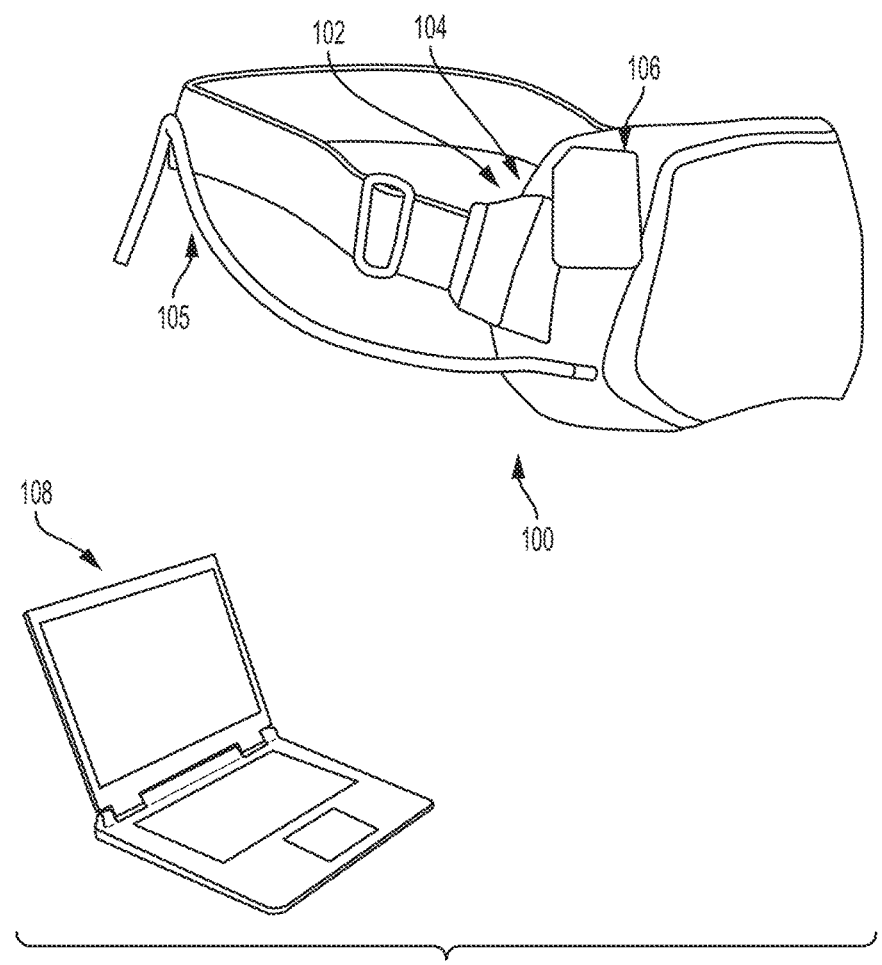
FIG. 1 is a graphic representation of one embodiment of a portable, high-speed, and high-resolution eye movement instrument capable of measuring eye movements to detect an mTBI.

The embodiments described below are merely exemplary and are not intended to limit the invention to the precise forms disclosed. Instead, the embodiments were selected for description to enable one of ordinary skill in the art to practice the invention.

In the United States alone, 3.2 million cases of mTBIs, such as concussions, occur annually from accidents, violence, military service, and sports. Upon the occurrence of an mTBI, an initial diffuse axonal injury (shearing) initiates a neurometabolic cascade of events resulting in membrane disruption and ionic imbalances. Diagnosis can occur at injury or in the following hours and days, and recovery takes days up to several weeks. For 20-30% of patients, mTBI leads to post-concussion syndrome (PCS), in which cognitive, somatic, and affective symptoms last for months or years. An estimated 1.6 million sport-related mTBIs occur annually in the United States. mTBIs such as concussions are receiving increased media and medical attention as the potential for serious long-term impacts becomes increasingly clear.

mTBI is among the most complex sports medicine injuries to diagnose and manage. Traditional structural imaging such as computed tomography (CT) and magnetic resonance imaging (MRI) cannot reliably detect such diffuse, low-level damage, is costly, and requires a trip to an imaging facility. In most cases, an athlete with suspected mTBI is checked on site, such as the sidelines of a football game, for symptoms and functioning. After 24 hours, mTBI is diagnosed through a tool such as the ImPACT™ test, a 10-variable neuropsychological battery also given at baseline, when a subject is unimpaired. This test is not viable as a rapid sideline test because of its length (30 minutes) and the need for a controlled testing environment. It is also susceptible to motivational factors (i.e., one's performance can be manipulated to increase or decrease the chance of being cleared to play).

Sport-related mTBIs are caused by rotary accelerations of the skull, making sport-related mTBIs unique and difficult to diagnose. For example, military mTBIs are oftentimes caused by blast injuries. A soldier's helmet and body armor may protect the soldier from flying debris, but not the air pressure wave from an explosion. The brain injuries caused by a blast wave, for example, and a sport-related injury caused by rotary accelerations of the skull are therefore different, and will result in different outcomes for post-injury eye movement.

The change from baseline is used in diagnostic and return to play decisions. The accuracy of these assessment methods is suspect, however. Acutely injured athletes may be unable to accurately realize or explain to others their symptoms. The composition of symptom questionnaires themselves can influence conclusions. Neuropsychological testing is influenced by age, intelligence, education, mental health, timing of injury, socio-economic status, practice effects and motivation. Both baseline and 'red flag' validity indicators are built into the ImPACT™ test, yet it is still possible to intentionally perform poorly at baseline in order to influence post-injury and return-to-play decisions. Another current test used to diagnose mTBI is the Sideline Concussion Assessment Tool (SCAT3), which is a written test given to a person thought to possibly have suffered an mTBI. However, such a test is also susceptible to bias from both players and coaches.

To accelerate healing and avoid long-term effects of an mTBI, excessive neural stimulation is to be avoided after an mTBI. Athletes are sidelined, and return to play occurs in a stepwise fashion. A previous mTBI increases the risk in future injuries, especially if initial symptoms are not completely resolved. Repeat mTBIs increase the risks for later dementia, Parkinson's disease and/or depression. Sports medicine professionals therefore feel significant pressure to rapidly and accurately (preferably on the field) diagnose and monitor recovery from an mTBI.

Basic classes of eye movements found to be indicative of an mTBI diagnosis include saccades, smooth pursuit, fixation, ocular following, vergence, and the vestibular ocular reflex (VOR). Saccades are rapid conjugate movements used when scanning a scene. Smooth pursuit involves the eyes tracking a moving object. Fixation keeps the fovea (central vision) on the stimulus. Ocular following stabilizes an image when the image moves. Vergence moves the eyes together or apart when something is moving in depth. Finally, VOR stabilizes an image by counter rolling the eyes when the head turns. Anatomical substrates for the planning and execution of these eye movements are well-mapped and complex.

For example, saccade generation and control includes: (1) cortical areas (e.g., frontal eye fields, parietal eye fields, and supplementary eye fields); (2) subcortical structures (e.g., superior colliculus, basal ganglia, and cerebellum); and (3) the brainstem (e.g., paramedian pontine reticular formation, cranial nerve nuclei III, IV, and VI). The anatomical pathways for smooth pursuit and vergence involve cortical, subcortical, and cerebellar brain structures. Ocular following requires visual cortex, extrastraite visual cortex (MT and MST), the cerebellum, basal ganglia, and the brain stem.

The preceding eye movements are under limited voluntary control. For example, with saccades, people choose where to look next but not how the eye gets there; a combination of saccade, vergence, and VOR movements could be used. Unlike choosing to move an arm quickly or slowly, eye kinematics are driven involuntarily by the brainstem. Smooth pursuit lag (keeping up or temporally falling behind a target) is involuntary and linked to the velocity of the stimulus, and ocular following is a machine-like involuntary reflex. In short, motivation plays no role in eye kinematics and dysfunction is a sign of neurological injury.

Oculomotor performance is sensitive to a wide variety of conditions, including head injury causing an mTBI. Smooth pursuit is related to schizophrenia, Parkinson's disease, progressive supranuclear palsy, hepatic encephalopathy and damage along the anatomical pathway (cerebellar disorders and large cerebral lesions). Attention deficit disorder demonstrates an increase in saccadic errors and delays, as does Parkinson's disease, Fetal Alcohol Syndrome, Tourette's syndrome, and brain lesions. Several vision-related brain areas can be affected during closed head injury, leading to oculomotor deficits.

Visual problems are a commonly-reported concussion sign. Among mTBI patients with vision symptoms, 90% exhibited one or more oculomotor dysfunctions, including problems with saccades and vergence. Among VA and military mTBI patients, 40% to 90% have oculomotor problems. Diffusion tensor imaging has been used to link smooth pursuit deficits in mTBI to white matter microstructural integrity.

A series of studies comparing mTBI patients with non-injured control subjects demonstrates the potential value of utilizing eye movement performance as a biomarker of mTBI related damage. Even without oculomotor deficits upon clinical exam, scores on a computerized test of saccade performance indicated cerebral dysfunction following an mTBI. Similarly, acute and chronic mTBI patients exhibited smooth pursuit deficits. A study combining saccade and smooth pursuit performance demonstrated the diagnostic value of oculomotor measures above and beyond neuropsychological testing. Studies also show that eye movement dynamics can track patient recovery and predict outcomes.

The present disclosure includes an on-site eye tracker for evaluating oculomotor performance as a biomarker of, for example, sport-related mTBIs. Unlike traditional laboratory-based eye trackers, the present apparatus is portable and usable outdoors even in bright sunlight. In one preferred embodiment, five classes of eye movements are monitored, as described further herein.

In one preferred embodiment of the present disclosure, an on-site eye tracker for evaluating oculomotor performance provides a series of eye tests targeted at users in a specified age range, for example the age range of users in professional, collegiate, high-school, and/or middle school level sports. mTBIs such as concussions, post-concussion management, and post-concussion prognosis are different depending on different age groups. The brain is quickly and radically developing throughout the teenage years. Therefore, in some preferred embodiments, the present disclosure is targeted at detecting concussions for person in the age group of between about 10 and about 30 years of age, and more preferably in the age group of between about 14 and about 26 years of age.

A portable, high speed, high spatial resolution eye tracker that is usable outdoors, aside from its potential value in sports, is contemplated to improve battlefield concussion testing and exams for high-risk occupations such as construction, mining, firefighters, etc. Because the test is rapid and repeatable, it can be used for monitoring recovery, even in situations where human bias or practice effects can interfere. With all component parts available and relatively inexpensive, the use of the device is contemplated in hospitals, schools, and other medical or high-risk settings.

Medical personnel will have better information on which to base critical and often urgent decisions regarding removal from and return to daily life. Researchers studying mTBI prevention and treatment will benefit from a tool that can document low-level injury and track recovery. In the same way that blood pressure cuffs revolutionized the measurement and care of certain conditions, an objective, repeatable, portable measure of concussion has the potential to play a role in revolutionizing concussion care.

Referring now to FIG. 1, an exemplary embodiment of a device to detect an mTBI is shown. Eye cover unit 100 comprises two microcameras 102 disposed within unit 100, such as MN43H 250-Hz HD cameras and/or Point Grey cameras. Two infrared LED lights 104 are mounted inside unit 100. In some embodiments, unit 100 can be a pair of virtual reality goggles, such as Oculus Rift Virtual Reality Goggles, or any other goggles or eye covering unit which shields substantially all external light from a user's eyes. Light from LED lights 104 hits the front of the subject's cornea and bounces back or reflects into microcameras 102. The location of this reflection (the first Purkinje image) relative to the pupil provides a measure of the eye's rotation or gaze angle.

Unit 100, microcameras 102, and infrared LED lights 104 are optionally powered by an external battery 106, such as a 4-ounce lithium ion battery. In the embodiment shown, unit 100 is substantially self-contained, and can securely rest on a user's head when straps 105 are secured over a user's head. Straps 105 can be adjustable and comprise any number of snaps, clips, pads and/or joints for comfort.

Eye movement pre-processing software is made from that type available on the Openeyes.org open source project in combination with a coding program, such as MATLAB. Each eye tracker can be operated by a standard notebook computer 108. In addition to generating visual stimuli, computer 108 stores eye movement and location records for later analysis. The entirety of the equipment, in some embodiments, is contemplated to fit in a container easily carried by one person, such as a backpack.

Communication between unit 100 and computer 108 could be wired, wireless, and/or proceed through one or more networks. Unit 100 can receive input commands and data directly via optional user controls physically disposed on unit 100 or from computer 108. Unit 100 can further output information to computer 108, by any wired, wireless, and/or network connection. Unit 100 and/or computer 108 can contain one or more physical memories to store data gathered during calibration, baseline tests, and/or diagnosis tests with unit 100. Such data could also be stored in a cloud-based storage medium.

Figure 2:
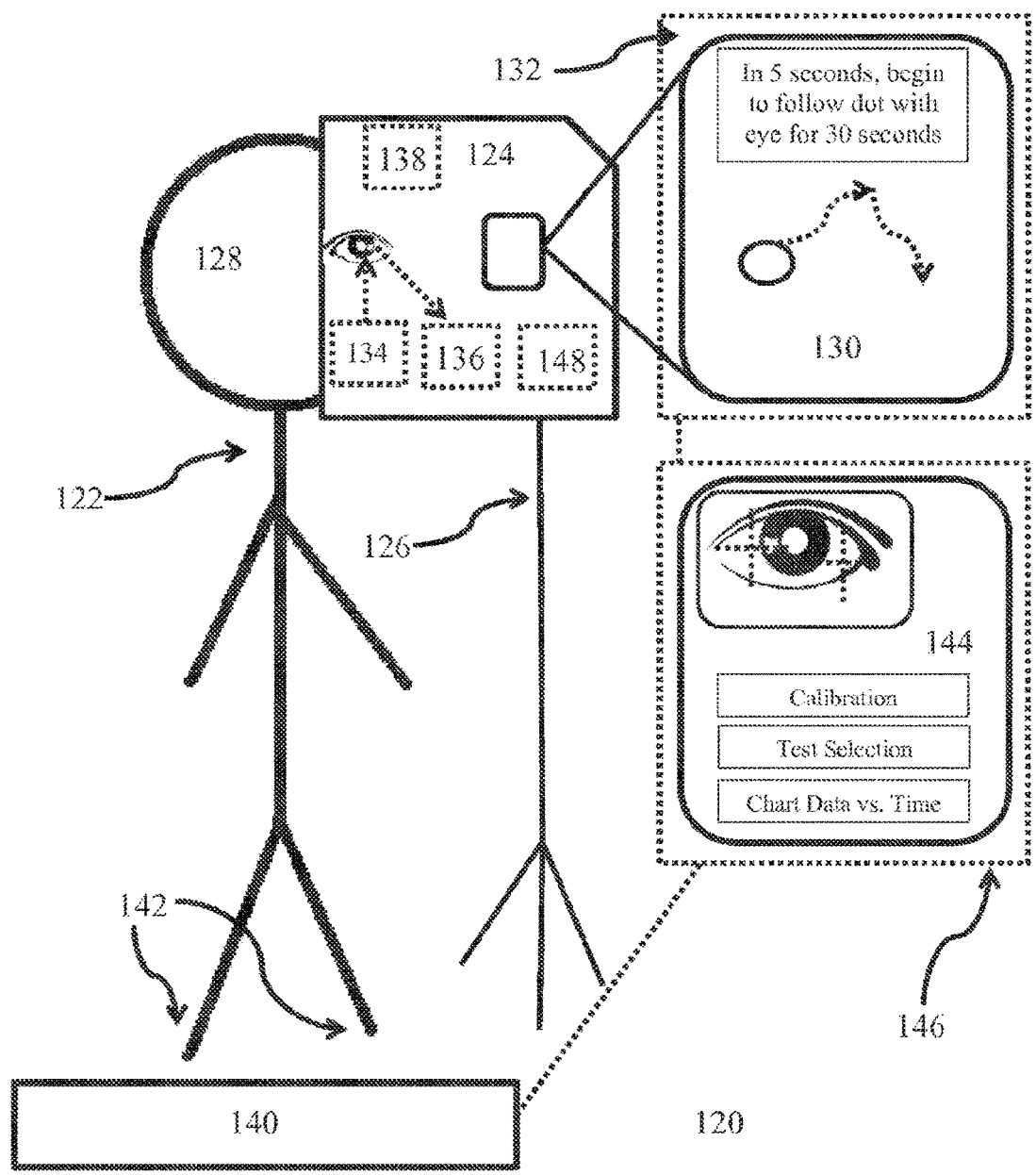
FIG. 2 is a conceptual diagram of an exemplary embodiment of a system for detecting an mTBI.

Referring now to FIG. 2, an exemplary embodiment of a system for detecting an mTBI is shown. System 120 is performed with a user 122 and includes a visualization unit 124, which is disposed on top of support structure 126 in certain embodiments, although support structure 126 is not necessary when the weight of unit 124 is low enough to be carried and held independently by user 122. In the embodiment shown, user 122 might be a student and/or athlete who has potentially suffered an mTBI, such as a concussion, in a sports game. In such a scenario, system 120 can be used to detect and diagnose an mTBI. However, user 122 may be any person who is not suspected of suffering a recent mTBI. In such a scenario, system 120 can be calibrated and/or can be used to measure and record the baseline score or scores of user 122 on one or more eye movement tests. In other embodiments, user 122 is a person previously diagnosed with an mTBI and is in recovery after the injury.

User 122 can be any male or female person, and in the embodiment shown user 122 is shown to be standing; however, system 120 is envisioned for use with user 122 disposed in any position including, but not limited to, sitting, leaning, and/or lying down. For example, if user 122 could not stand, but only sit or lie down, a compact, completely wearable embodiment similar to that of unit 100 of FIG. 1 may be used for mTBI testing.

Head 128 of user 122 is disposed partially within visualization unit 124. Any comfortable configuration for user 122 to partially dispose head 128 within visualization unit 124 is envisioned. Head 128 of user 122 need not be mounted to or coupled with visualization unit 124; instead, user 122 may simply rest head 128 within unit 124. For example, visualization unit 124 can include any combination of one or more headrests, chinrests, straps (such as straps 105 in FIG. 1), pads, flaps, or covers. In the embodiment shown, visualization unit 124 is a substantially cube-shaped unit, but in other embodiments visualization unit 124 could be other shapes, such as substantially oval-shaped or shaped like goggles such as unit 100 in FIG. 1.

Visualization unit 124 preferably allows user 122 to comfortably rest head 128 while substantially blocking external light from the eyes of user 122. At least one user screen 130, one infrared LED light 134 (described further below with reference to FIG. 3), and one eye tracker camera 136 are disposed within unit 124. Thus, the configuration of unit 124 should provide user 122 with a comfortable view of screen 130, and should also provide the at least one camera 136 and one infrared LED light 134 a direct line of sight to at least one eye of user 122.

As noted, visualization unit 124 includes user screen 130 disposed within unit 124, which is viewable by user 122 when head 128 is partially disposed within unit 124. In the embodiment shown, there is only one user screen; however, in other embodiments, more or fewer user screens could be utilized. User 122 may be looking directly at screen 130 when head 128 is partially disposed within unit 124, or user 122 might view screen 130 via one or more mirrors disposed at angles relative to screen 130 which enable user 122 to view screen 130 as if it were directly in front of head 128. In one embodiment, screen 130 is capable of displaying stationary or moving text and/or images in both black and white and/or color. Screen 130 is also capable of displaying to user 122 commands for calibration, baseline, and mTBI testing, described further below. For example, screen 130, in the embodiment shown in FIG. 2, instructs user 122 to begin to follow the hollow dot shown on screen 130 in 5 seconds and to do so for 30 seconds.

In some embodiments, screen 130 might be the screen of a computing device 132, for example a notebook computer or tablet computer. Screen 130 may be connected to one or more computing devices by any wired, wireless, and/or network connection. For example, computing device 132 may be disposed within visualization unit 124 proximate to screen 130, or it may be disposed separately from unit 124 and screen 130. Computing device 132 can have any combination of processors, physical or cloud-based memories, and/or databases. Computing device 132 is capable of accepting user input commands and user input data, and is capable of outputting data to screen 130 or other computing devices by any combination of wired, wireless, and/or network connections.

Visualization unit 124 further includes at least one light source, preferably one infrared LED light 134, and at least one camera 136, such as, but not limited to, MN43H 250-Hz HD cameras. During operation of system 120, which can include calibration, baseline testing, and/or mTBI detection, light from LED light 134 is directed toward the front of at least one cornea of one eye of user 122 and bounces back or reflects into camera 136. The location of this reflection (the first Purkinje image) relative to the pupil of user 122 provides a measure of the eye's rotation or gaze angle to computing device 132.

In some embodiments, visualization unit 124 is substantially or completely battery-powered. Any or all of the components of visualization unit 124 can be powered by one or more batteries. One such exemplary battery is a custom rechargeable 12V NiMH battery pack which powers screen 130 and infrared LED light 134. Such an exemplary battery has a runtime of about 1.5 hours, but any combination of batteries and/or hard-wired power is envisioned to provide for a necessary runtime of visualization device 124 and/or system 120.

Visualization unit 124 also includes audio unit 138, which in the embodiment shown is disposed on the side of unit 124, but in other embodiments could be disposed elsewhere on unit 124, and/or could be disposed separately from unit 124. Audio unit 138 can include at least one input device, such as a microphone, and at least one output device such as a speaker and/or retractable headphones for user 122. In the embodiment shown, unit 138 is capable of receiving audio input, such as the voice of user 122, and is capable of outputting audio, such as the commands shown on screen 130. For example, audio unit 138 might output sound stating "In 5 seconds, begin to follow dot with eye for 30 seconds, say 'ready' when ready." In response, user 122 might state "ready" into a microphone or similar device to begin a calibration, baseline test, or test for an mTBI. Any combination of wired, wireless, and/or network technology is envisioned for use with audio unit 138.

In the embodiment shown, visualization unit 124 is disposed on top of support structure 126, shown as a tripod. In other embodiments, support structure 126 could be a bipod, monopod, and/or any other structure capable of supporting visualization unit 124, so that it is stable for use by user 122. However, structure 126 is optional, and unit 124 can be designed such that it is light-weight, compact, and wearable on head 128 of user 122 by any combination of one or more straps, grips, helmets, and/or glasses. For example, unit 100 of FIG. 1 is shown with straps 105, and could be used without support structure 126.

In the exemplary embodiment of FIG. 2, system 120 includes optional balance board 140 for use by user 122. User 122 is disposed in a standing position on balance board 140. In one embodiment, balance board 140 interprets the position and balance of user 122 by sensing the pressure applied at different points of feet 142 of user 122. For example, balance board 140 can interpret if user 122 leans forward, backward, to the left, and/or to the right during a calibration, baseline, and/or mTBI test. Balance board 140 can also interpret if user 122 wobbles, sways, shakes, stands still, pivots, and/or shifts during the aforementioned tests. Balance is tied to mTBI, and in some users balance will suffer during and after an mTBI. Balance board 140 can be, in some embodiments, a commercially-available Nintendo Wii Balance Board.

As noted, balance board 140 is optional, and need not be used with system 120. However, the difference measured in the balance of user 122 between a baseline test, in which the user has not suffered an mTBI, and in an mTBI diagnosis, in which user 122 has suffered an mTBI, can be helpful to supplement the diagnosis of mTBI when combined with the tests conducted on the eye(s) of user 122. In other embodiments, other means capable of measuring and tracking the balance and/or stability of user 122 are envisioned to be used alone or in combination with balance board 140, such as the Kinect device for use with the XBOX 360 system. For example, user 122 might stand on the ground or floor, or sit in a chair, and a motion-detecting device, such as, for example, the Kinect device, would detect the left-right, forward-rearward, circular, sway and/or other motion of user 122 during calibration, baseline, and/or mTBI tests. The comparative analysis of the motion of user 122, between a baseline (when user 122 is not impaired by an mTBI) and a potential mTBI, can help supplement a diagnosis of mTBI in addition to the variety of eye tests described herein.

Balance board 140, or similar balance measuring devices, could be used to execute additional tasks for user 122 which focus only on the user's balance, such as requiring the user 122 to place his or her hands on the hips while putting feet 142 together in substantial darkness. In some embodiments, user 122 could be instructed to place the non-dominant foot forward and balance. In other embodiments, user 122 could be instructed to stand on the non-dominant foot and raise the dominant foot. A concussed individual is more likely to fall, wobble, or sway in such situations, which would be tracked and recorded by balance board 140 or a similar balance measuring device.

System 120 includes operator screen 144 disposed outside of visualization unit 124, and screen 144 is viewable by any operator or operators before, during, or after system 120 is used to perform any test, including, but not limited to, calibration, baseline, and/or mTBI tests. In the embodiment shown, there is only one operator screen; however, in other embodiments, more or fewer operator screens could be utilized. In the embodiment shown, operator screen 144 provides a view of one eye of user 122 with two cross-hatches, which move to follow the movement of the eye of user 122. Screen 144 is capable of displaying stationary and/or moving text and/or images in both black and white and/or color. Screen 144 is also capable of displaying to any operator commands for calibration, baseline, and mTBI testing, described further below. For example, screen 144, in the embodiment shown in FIG. 2, offers the operator the ability to calibrate the device, select a test, such as a baseline or mTBI detection test, or chart stored data vs. time.

In some embodiments, screen 144 might be the screen of a computing device 146, for example a notebook computer or tablet computer, and screen 144 can be a touch-screen, capable of accepting operator commands by touch. Screen 144 may be connected to one or more computing devices, such as computing device 132, by any wired, wireless, and/or network connections. For example, computing device 146 may be disposed proximate visualization unit 124, or it may be disposed separately from unit 124. Computing device 146 can have any combination of processors, physical or cloud-based memories, and/or databases. Computing device 146 is capable of accepting user input commands and user input data, and is capable of outputting data to screens 130 and/or 144, or other computing devices by any combination of wired, wireless, and/or network connections.

Computing device 146 is also capable of receiving data from, and outputting data to, unit 124 and balance board 140. Furthermore, computing devices 132 and 146 are optionally capable of storing data gathered from unit 124 and balance board 140 for analysis, processing, and display of said data. In the embodiment of FIG. 2, system 120 also includes optional user controls 148 disposed on the side of visualization unit 124. Such optional controls may be a touchscreen, keypad, individually shaped keys, or any other suitable means for a user to input data and/or input a response to a request displayed on screen 130. Controls 148 need not be disposed on unit 124, but instead could be a separate touchpad, keypad, one or more buttons, and/or any combination of these connected by any wired, wireless, and/or network connection to computing device 132 and/or 146.

Optional user controls 148, in one example, might provide user 122 with an up arrow to press when user 122 sees a stimulus move upward on screen 130, and a down arrow to press when user 122 visualizes a stimulus move downward on screen 130. In another example, user 122 may input certain data into controls 148 to signify preparedness for a calibration, baseline test, and/or mTBI test.

In one exemplary embodiment, the oculomotor exam provided to user 122 on screen 130 consists of 5 tasks described below to monitor five classes of eye movement. For each, stimuli appear on screen 130 as black dots against a 50% gray background. User 122 carries out such tasks on either the device of FIG. 1 or the system of FIG. 2. In the first case, user 122 slides the pair of goggles over his or her face and tightens it to the head. In the second case, user 122 places head 128 partially within visualization unit 124, optionally while standing on balance board 140.

The eye tracker device is then calibrated to the geometry of a subject's eyes. Referring to the system embodiment of FIG. 2, for calibration, screen 130 instructs user 122 to fixate either one or both eyes on a dot at nine known locations on screen 130. Following calibration, screen 130 provides instructions for the first task and for each task thereafter. The series of five tasks is presented twice during each exam session and results in 22 measured variables as shown in Table 1 below. Including the repeated tasks, the exam takes roughly five minutes to complete.

In the ocular following task, user 122 is instructed to "look at the dot." After a brief delay, the dot disappears and screen 130 is covered (whole field view) with stable random dots. This stimulus field then begins linearly drifting left or right for 200 ms at a moderate speed (31°/s). Twenty of these rapid trials are completed. Under this scenario, the brain attempts to stabilize the image by rotating the eye with the stimulus, resulting in an involuntary, machine-like gaze stabilization reflex called ocular following (the early optokinetic reflex). Both response time and eye velocity are measured.

Finally, in the dynamic random dot task, after fixating on a dot, user 122 sees a field of dynamic random dots that look like white noise. A floating square defined only by binocular disparity (the difference in image location of an object seen

TABLE 1

Ocularmotor performance tasks and variables measured

| Self-Paced Saccade Task | | Sinusoidal Pursuit Task | | Step Ramp Pursuit Task | | Ocular Following Task | | Dynamic Random Dot Task |
|---|---|---|---|---|---|---|---|---|
| 1. | Saccade frequency | 1. | RMS error | 1. | Response time | 1. | Response time | 1. Psychophysics threshold |
| 2. | Peak velocity | 2. | Gain | 2. | Gain | 2. | Eye velocity | |
| 3. | Amplitude | 3. | Lag | 3. | Lag | 3. | Eye acceleration | |
| 4. | Accuracy | 4. | Catch-up saccade frequency | 4. | Catch-up saccade | | | |
| 5. | Secondary saccades | | | 5. | Eye acceleration | | | |
| 6. | Post-saccadic drift amplitude | | | | | | | |
| 7. | Post-saccadic drift duration | | | | | | | |
| 8. | Intersaccadic interval | | | | | | | |
| 9. | Rate of change of intersaccadic interval | | | | | | | |

First, in the self-paced saccade task, user 122 is instructed to "look back and forth between the two dots as many times as you can" as two stationary (static) stimuli 11 degrees apart are displayed on screen 130 for 30 seconds. This task measures saccade frequency (number of saccades made in 30 seconds), kinematics (e.g. peak velocity vs. amplitude), accuracy (geometric distance between the eye position and the stimulus following the primary saccade to a target), secondary involuntary corrective saccades (mini saccades made after the primary saccade in order to achieve better foveation of the stimulus) and post-saccadic drift (the size and speed of eye motion after the primary saccade has terminated). As a measure of fatigue, the intersaccadic interval and the intersaccadic interval as a function of time (rate of change) are also calculated, optionally by computing device 146.

Next, in the sinusoidal pursuit task, the user 122 is instructed to "follow the moving dot" as a single dot appears on the left side of screen 130. After a brief period of fixation, the stimulus moves sinusoidally at speeds of 0.5, 0.75, 1.25, and 1.5 Hz (ten seconds each in random order presented twice). The amplitude of the sinusoid is 10 degrees. The sinusoidal pursuit task is one of the most commonly used predictive (meaning the subject needs to predict the future location of the stimulus) tasks. It measures pursuit gain (how well eye motion matches stimulus motion) and lag (whether eye motion falls behind the stimulus).

In the step-ramp pursuit task, after fixating on a central spot displayed on screen 130, user 122 is instructed to "follow the moving dot." The stimulus jumps to the left or right and drifts towards the center. The size and speed of the jump are carefully calculated to elicit pursuit eye movement without saccade contamination. This task measures response time, gain, and lag. Introduced by Rashbass, it is a commonly used task for eye movement detection.

by the left and right eyes due to horizontal separation of the eyes) will appear in front or behind this field. User 122 then sees "Press the up arrow when the floating square is in front of the background. Press the down arrow when the floating square is behind the background. If you are unsure, take a guess." User 122 would press such arrows on optional user controls 148. To discriminate a 3D stimulus in this manner requires precise eye alignment at the correct depth plane. It is a standard clinical optometric tool (RANDOT™).

Figure 3:
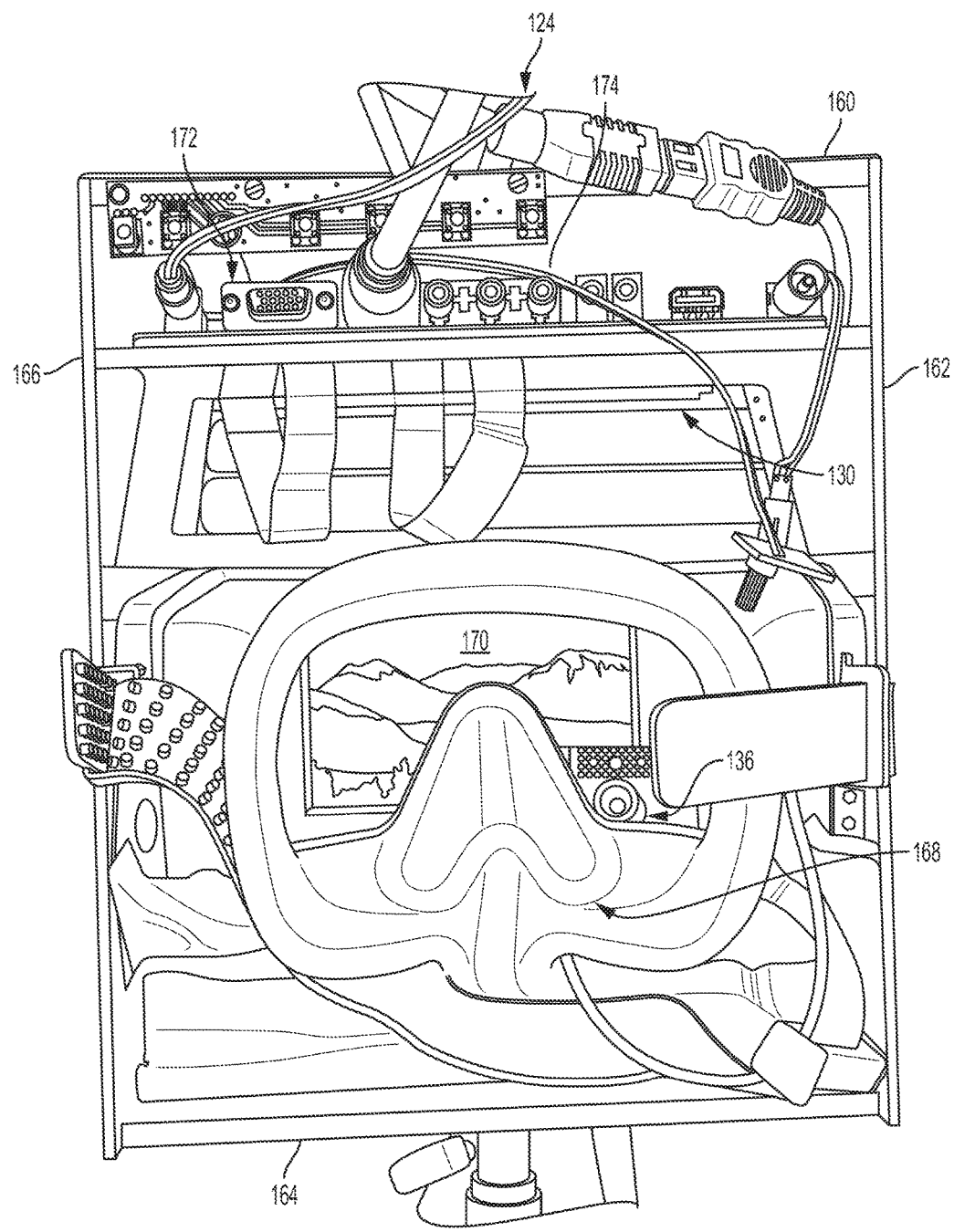
FIG. 3 is an inside view of one embodiment of visualization unit 124 of FIG. 2.

Referring now to FIG. 3, an inside view of one embodiment of visualization unit 124 of FIG. 2 is shown. Unit 124 includes a first side 160, a second side 162, a third side 164, and a fourth side 166. In the embodiment shown, unit 124 is substantially rectangular; however, in other embodiments sides 160, 162, 164, 166 may form any suitable shape, so long as unit 124 substantially blocks light from outside of unit 124 from entering within unit 124 while a user's head is partially disposed within unit 124. Unit 124 may be formed of any material known in the art such as metal, plastic, and/or any high-strength, light-weight composite material. A portable, lightweight example of unit 124 is provided in FIG. 1 as unit 100. Unit 124 could include straps (not shown) similar to straps 105 of FIG. 1 such that unit 124 could be worn by a user without a support and without being held by user 122 or an operator.

FIG. 3 also shows head support 168 to support a user's head while unit 124 is in use. Any suitable support which provides stability and support to a user's head with sufficient comfort is envisioned, such as a pad, pillow, strap, and/or any other means known in the art. Head support 168 can be a tightly-fitting rubber mask, or tightly-fitting mask made of a similar material, such as a scuba mask. The seal of such a mask blocks outside light, allowing, in some embodiments, operation in direct sunlight conditions. Camera 136 is shown positioned proximate support 168, so that when light, optionally from an infrared LED light, is reflected off of a user's cornea, the light bounces back or reflects into camera 136. The location of this reflection (the first Purkinje image) relative to the pupil of user 122 gives a measure of the eye's rotation or gaze angle.

In the embodiment shown, screen 130 is disposed above support 168 and camera 136, and the image displayed on screen 130 is reflected into mirror 170. In other embodiments, no mirrors are necessary if screen 130 itself is positioned directly in front of the user's eyes, but still in other embodiments, more than 1 mirror can be used. By placing screen 130 closer to a user's head, in some embodiments, the moment arm of unit 124 is decreased, and thus unit 124 is easier for a user to wear on his or her head.

In FIG. 3, mirror 170 displays a scene from nature reflected from screen 130. Such a scene from nature, or a similarly relaxing image, is displayed to the user, in some embodiments, when the user first uses visualization unit 124 and/or between tests to alleviate any feeling of nervousness or of claustrophobia. A relaxing scene also allows a user's eyes to rest in between tests. Still referring to FIG. 3, input-output components 172, 174 are shown disposed near screen 130. In some embodiments, components 172, 174 are part of the same computing unit of screen 130, for example a tablet computer. In other embodiments, components 172, 174 are added separately to unit 124. Components 172, 174 allow for any wired audio, visual, and/or control connection between visualization unit 124 and a second computing device, such as a control computer.

Figure 4:
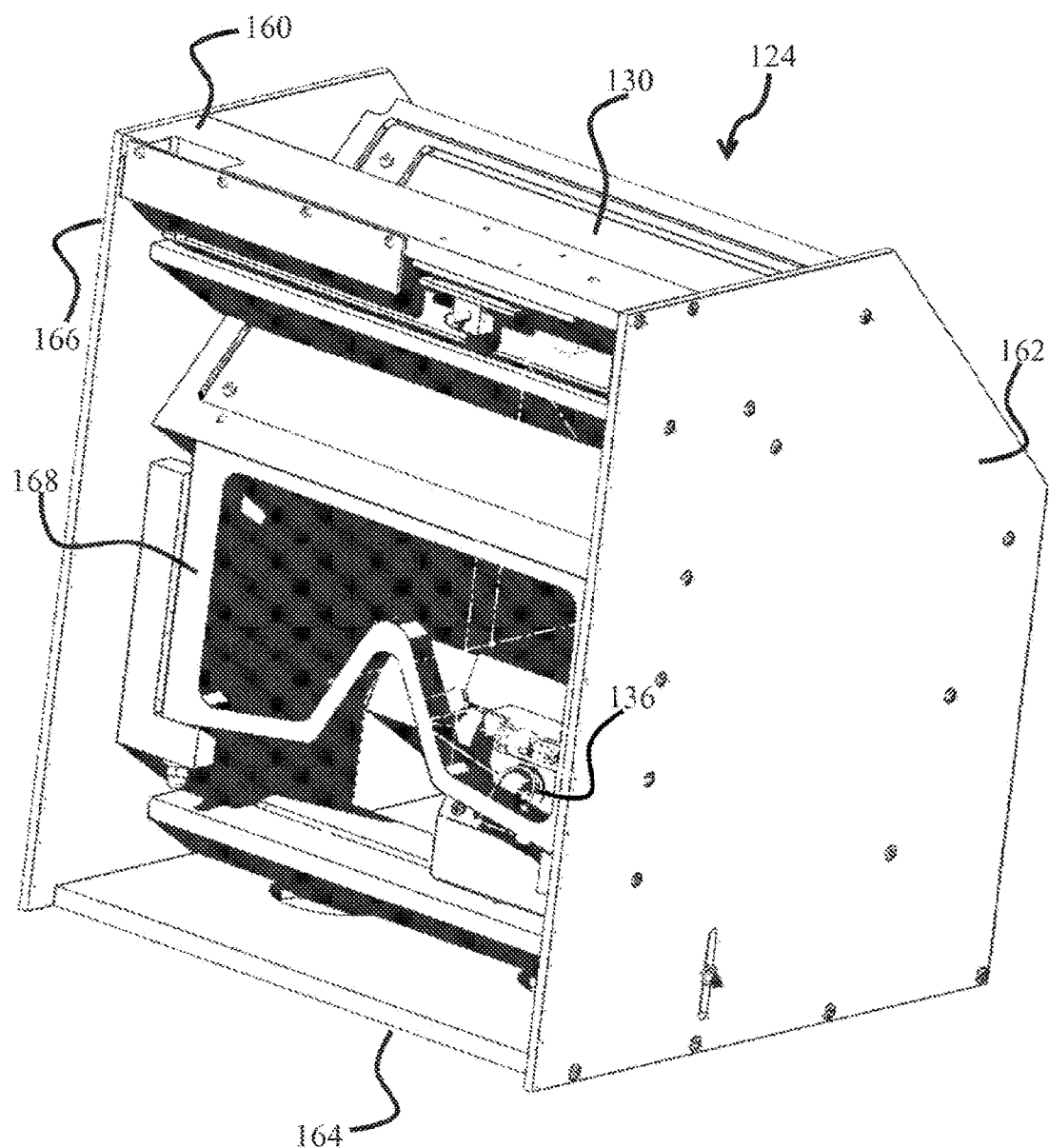
FIG. 4 is a perspective view of one embodiment of visualization unit 124 of FIG. 2.

Referring now to FIG. 4, a perspective view of one embodiment of visualization unit 124 of FIG. 2 is shown. As described above, unit 124 includes a first side 160, a second side 162, a third side 164, and a fourth side 166. In the embodiment shown, unit 124 is substantially rectangular; however, in other embodiments sides 160, 162, 164, 166 may form any suitable shape, so long as unit 124 substantially blocks light from outside of unit 124 from entering within unit 124 while a user's head is disposed within unit 124. Unit 124 may be formed of any material known in the art such as metal, plastic, and/or any high-strength, light-weight composite material. A portable, lightweight example of unit 124 is provided in FIG. 1 as unit 100. Unit 124 could include straps (not shown) similar to straps 105 of FIG. 1 such that unit 124 could be worn by a user without a support and without being held by the user or an operator.

FIG. 4 also shows head support 168 to support a user's head while unit 124 is in use. Any suitable support which provides stability and support to a user's head with sufficient comfort is envisioned, such as a pad, pillow, strap, and/or any other means known in the art. Camera 136 is shown positioned proximate support 168, so that when light, optionally from an infrared LED light, is reflected off of a user's cornea, the light bounces back or reflects into camera 136. The location of this reflection (the first Purkinje image) relative to the pupil of user 122 gives a measure of the eye's rotation or gaze angle.

In the embodiment shown, screen 130 is disposed above support 168 and camera 136, and the image displayed on screen 130 is reflected into mirror 170 (shown in FIG. 3). In other embodiments, no mirrors are necessary if screen 130 itself is positioned directly in front of the user's eyes, but still in other embodiments, more than 1 mirror can be used. By placing screen 130 closer to a user's head, in some embodiments, the moment arm of unit 124 is decreased, and thus unit 124 is easier for a user to wear on his or her head.

Figure 5:
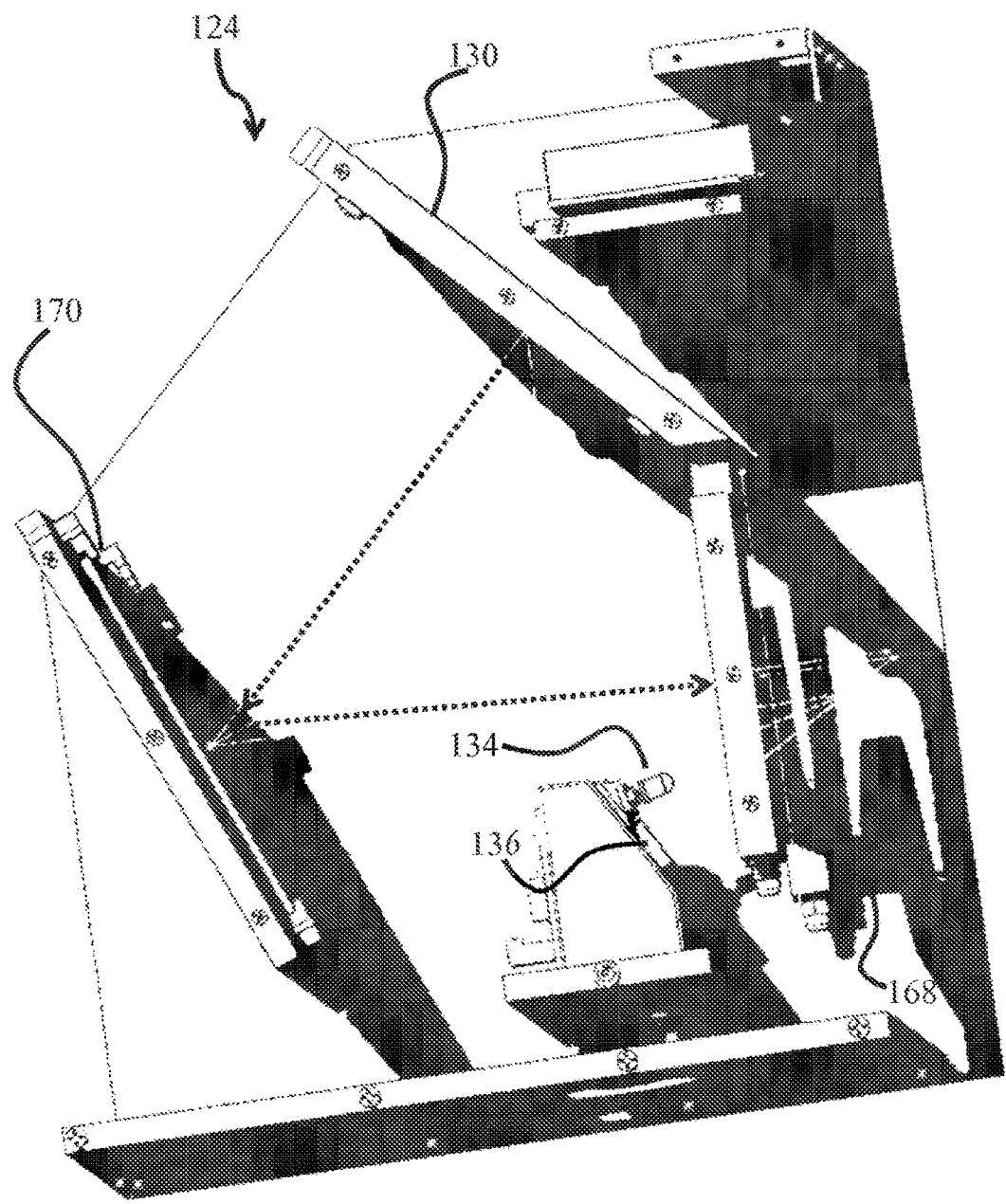
FIG. 5 is a perspective cut-away view of one embodiment of visualization unit 124 of FIG. 2.

Referring now to FIG. 5, a side cut-away view of one embodiment of visualization unit 124 of FIG. 2 is shown. As noted, visualization unit 124 further includes at least one infrared LED light 134, which in other embodiments might be another light source capable of reflecting light off of a user's eye into camera 136. In the embodiments described herein, the user of visualization unit 124 does not see the light reflecting off of the user's eye.

There is also at least one eye tracker camera 136, such as, but not limited to, a MN43H 250-Hz HD camera. During operation of unit 124, which can include calibration, baseline testing, and/or mTBI detection, light from infrared LED light 134 hits the front of at least one cornea of one eye of a user and bounces back or reflects into camera 136. The location of this reflection (the first Purkinje image) relative to the pupil of a user provides a measure of the eye's rotation or gaze angle to computing device 132.

As noted, visualization unit 124 includes user screen 130 disposed within unit 124 and viewable by user 122 when head 128 is partially disposed within unit 124. In the embodiment shown, screen 130 is disposed above support 168 and camera 136, and the image displayed on screen 130 is reflected into mirror 170. In other embodiments, no mirrors are necessary if screen 130 itself is positioned directly in front of the user's eyes, but still in other embodiments, more than one mirror can be used. By placing screen 130 closer to a user's head, in some embodiments, the moment arm of unit 124 is decreased, and thus unit 124 is easier for a user to wear on his or her head.

EXAMPLES

In one exemplary protocol executed on system 120 of FIG. 2, two saccadic eye movement exams (two tasks), two pursuit eye movement exams (within one task), and one Optokinetic eye movement exam (one task) are conducted. The complete exam takes only seven minutes. In other exemplary protocols, the complete exam may take more or less than seven minutes, depending on the number and length of the tests given to a user.

First, system 120, is set up for use by user 122. In some embodiments, system 120 is easily portable and can be set up near user 122 without user 122 having to travel. In some embodiments, setup can take as few as between one and two minutes. User 122 then places head 128 partially within unit 124 and rests head 128 on a support, optionally similar to head support 168 of FIG. 3. Straps similar to straps 105 of FIG. 1, or other securing means, can also be used to secure head 128 of user 122 to visualization unit 124. At this initial stage, a pleasant nature scene, or similarly relaxing scene, optionally can be displayed on screen 130 (and projected onto optional mirror 170) to alleviate user 122 of any feeling of claustrophobia or nervousness.

Next, an operator or operators open exam software on a laptop computer, or a similar second computing device 146, described above. Alternatively, and as described above, the software to run the eye exams could be fully contained within a wearable visualization unit, such as that provided in FIG. 1, as no second computing device is required. In some embodiments, operator's screen 144 is the screen of a light-weight, portable computing device, such as a tablet computer or a mobile smart phone. In some embodiments, the laptop computer or computing device provides a touch-screen, capable of accepting operator commands by touch. Screen 144 may be connected to one or more computing devices by any wired, wireless, and/or network connections.

Eye movement pre-processing software is optionally made from that type available on the Openeyes.org open source project in combination with a coding program, such as MATLAB. Alternatively, a scientific computing software language such as MATLAB can be used to create eye movement software by itself. In addition to generating visual stimuli for user 122, the operator's computer stores eye movement and location records for later analysis.

Next, the user's identification information is entered into the software. The user's identification information includes in some embodiments the user's name, age, height, weight, gender, sport played, baseline test date(s), time since suspected mTBI, previous mTBIs, occupation, and/or any other relevant information for diagnosis of an mTBI. In some embodiments, the information of one user, such as an individual sport player, or the information of more than one user, such as a sports team, can be stored within system 120. In such a way, if an mTBI must be diagnosed quickly, the stored information of a particular user can be retrieved by system 120. Then, both operator screen 144 and user screen 130 inside visualization unit 124 switch over to a view of what eye tracker camera 136 sees. Such a view from eye tracker camera 136 is provided in FIG. 6.

The operator and user 122 see the same camera view, allowing them to discuss any required adjustments before the experiments begin. One common adjustment is for the subject to move their face in head support 168, or a similar face mask or support, to provide a clearer view of the eye. Another adjustment performed is to change the brightness of infrared LED light 134. In one embodiment, a custom circuit board with a direct-current adjustment dial is installed on the outside of visualization unit 124 to adjust the brightness of infrared LED light 134.

Figure 6:
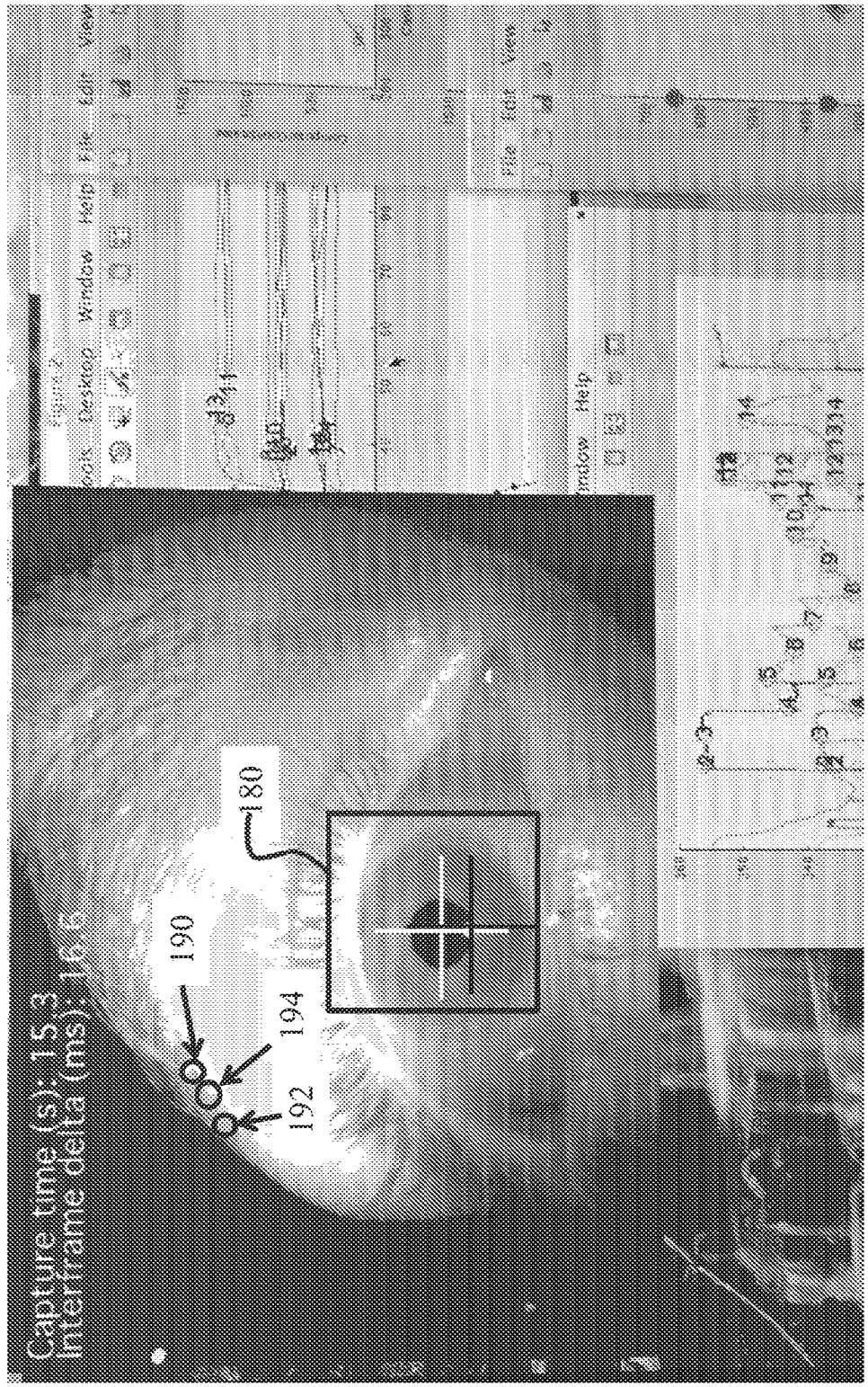
FIG. 6 is a screen shot of an exemplary operator screen when one embodiment of visualization unit 124 of FIG. 2 is in use.

After these adjustments, a second, side-by-side image of the eye of user 122 is displayed on operator screen 144 next to a simple graphical interface, as shown in FIG. 6. The operator then draws target 180 around the iris of user 122 using a computer mouse, trackpad, stylus, and/or similar device. Alternatively, target 180 could be drawn using a touchscreen. Target 180 provides a discrete area with coordinates to the real-time software within which to search for the pupil and corneal reflection of user 122. Target 180 also delineates to the software where not to search (outside of target 180) during the experiments.

Next, the operator indicates to the software to begin the calibration of visualization unit 124. In alternative embodiments, for example a completely portable and self-contained system such as that shown in FIG. 1, user 122 could accept instructions after prompting from the software to begin calibration. Instructions are displayed on user screen 130, and user 122 reads the instruction for the calibration task, such as, for example: "Please carefully and accurately follow the dot". In some embodiments, the instructions are verbally restated by the operator to user 122 to ensure the calibration is accurate.

Figure 7:
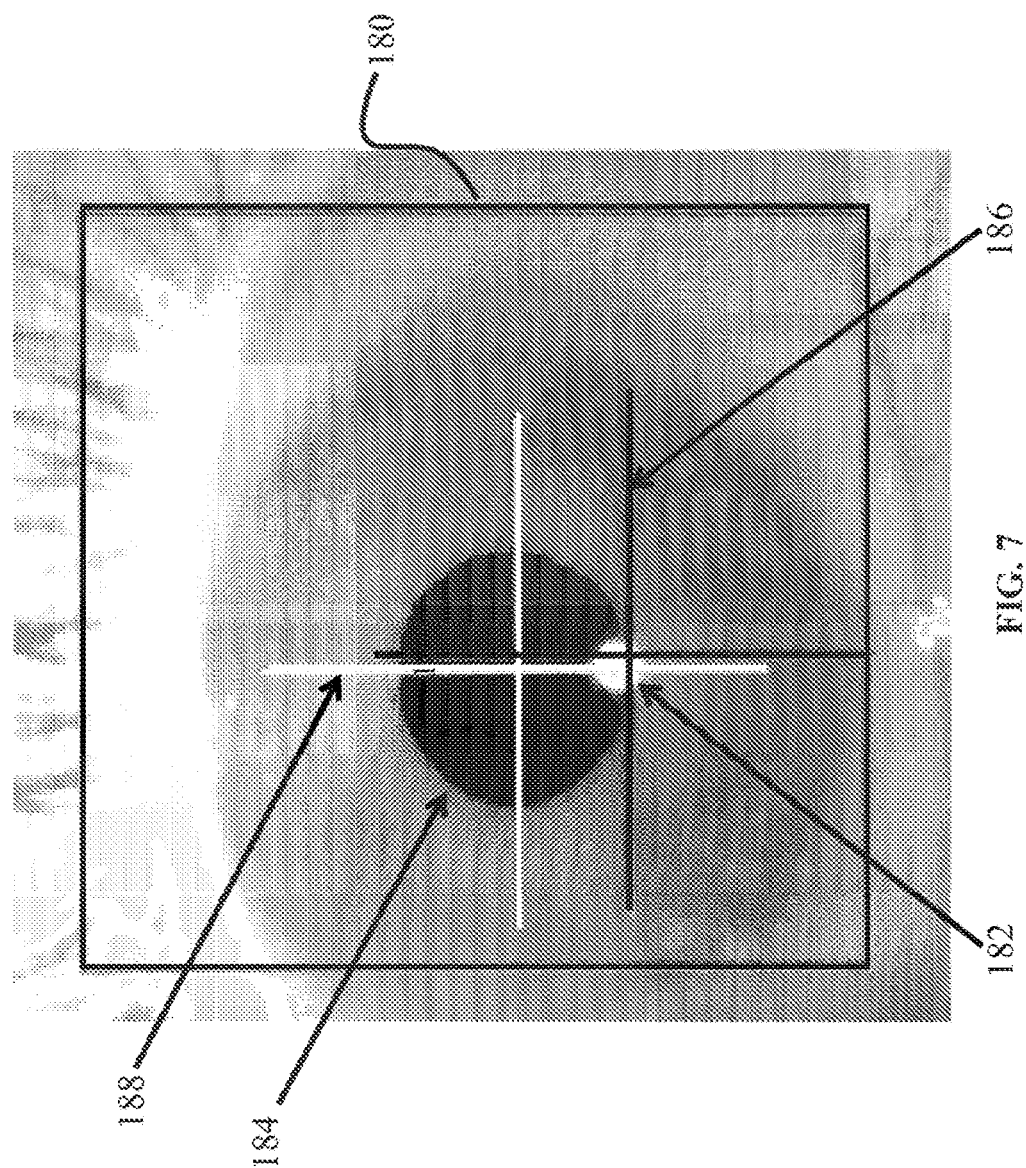
FIG. 7 is an enlarged screen shot of a user's eye from the exemplary operator screen of FIG. 6.

Once user 122 and/or the operator have accepted to begin calibration, a 13-point calibration task begins. In this task, user 122 carefully follows a moving dot as it "steps" or "jumps" to one of 13 locations on user screen 130. While user 122 is carefully following the jumping dot, the operator is watching the eye of user 122 in real time on operator screen 144. Visualization unit 124 operates with camera 136 tracking the corneal reflection of infrared LED light 134, in one particular embodiment a 950 nm infrared LED, and with camera 136 tracking the location of the pupil of user 122. Referring now to FIG. 7, in order to aid the operator, the bright corneal reflection 182 is false colored and the black of pupil 184 is also false colored. Crosshair 186 is then drawn through the center of the corneal reflection and crosshair 188 is drawn through the center of the pupil. Such a false colored display and cross hairs 186, 188 allow the operator to determine whether a sufficient eye movement recording for proper data analysis is being acquired during the eye exams.

After executing the calibration with the grid of 13 points, user 122 sees on screen 130 a pleasant nature scene while second computing device 146 quickly analyzes the pupil and corneal reflection movements, and then calculates a calibration mapping function. Light from infrared LED light 134 hits the front of the cornea of user 122 and bounces back or reflects into camera 136. The location of this reflection (the first Purkinje image) relative to the pupil gives a measure of the eye's rotation or gaze angle.

Next, a 13-point calibration validation task is executed. The calibration task above is repeated to validate the calibration. During this task and all subsequent tasks, the false colored view of camera 136 with cross hairs 186, 188 is displayed on operator screen 144. This allows the operator to monitor the data acquisition. Superimposed on top of the image provided by camera 136 are locators showing the real-time location of stimuli 194 for the subject to look at and the current location of the eye 190, 192 as shown in FIG. 6. Once again, FIG. 6 provides one embodiment of a display for operator screen 144. Locators 190, 192, and 194 provide additional feedback to the operator about the quality of data acquisition and the user's performance of the task.

In the embodiment shown, locator 194 is the location of the stimulus during a test or task. For user 122, the stimulus is a white dot on a black background on screen 130, except for the optokinetic stimulus. In the optokinetic task, stimuli are white and black dots on a grey background. Since the experiment is done on a 50% grey background, the beginning of the trial presents a white circle on a 50% grey background.

Locators 190, 192 are both a representation of where the eye of user 122 is presently looking during a test or task. Normally, there are conjugate eye movements between both eyes of a user, so both eyes are presumably looking at the same place. There are two locators 190, 192 in the embodiment shown, because the real-time eye tracking is being done with and without a drift correction. Since user 122 might move during the experiment, locator 190 is corrected for drift, and this is shown by locator 192. Locator 190 is the non-drift corrected, real-time calculated/estimated position of where user 122 is presently looking. Because locators 190,192 are generated in real-time every 16 milliseconds, the eye position is smoothed so as not to appear jittery or shaky. The location of the eye is averaged over the preceding 3 video frames (i.e., 12 ms*3=48 ms). This averaging prevents any shaking in the image, but does mean the feedback cursor is slightly behind the real location of the eye as shown on operator screen 144. The real analysis of the measured variables to determine an mTBI does not use the averaging technique, only the visual real-time feedback. Locators 190, 192, and 194 help the operator determine whether user 122 is doing the tasks correctly, and is not confused, asleep, or otherwise impaired from performing the presented tasks.

After the calibration validation task, the software prompts the operator to determine if he or she is satisfied with the calibration of user 122. If the operator responds "yes," then the software asks the operator to turn on the optional balance board 140, for example a Wii Balance Board. Between every task, pleasant nature scenes are shown to user 122 on screen 130 to help alleviate claustrophobia and give user 122 some time, preferably between 10-60 seconds, to rest. Before data collection begins on every task, the instructions for the task are displayed on screen 130 for user 122. The software then pauses and asks the operator to check in with user 122, making sure user 122 understands the instructions and is ready to proceed. Such pauses also allow user 122 to do other things (e.g., readjust their positioning or scratch an itch).

In some alternative embodiments, to calibrate a device of the present disclosure and/or ensure its accuracy, a simple comparison of the sideline eye tracker and a 'gold standard' eye tracker such as the EyeLink 2000 can be performed on each of the oculomotor performance variables. A mathematical correction corrects for expected minor calibration issues (skewing) between eye trackers. The Pearson's r correlation is then examined for each variable (e.g., peak velocity, pursuit lag, etc.). A Bland-Altman analysis is also performed. Because psychophysics toolbox stimulus generation code underlies both the EyeLink 2000 and the sideline eye tracker of the present disclosure, stimulus generation is not a likely source of variation.

After calibration and calibration validation, a self-paced saccade task, which lasts about 20 seconds, is conducted on user 122. In such a task, two static white circles on a black background are placed to the left and right edge (10% and 90%) of user screen 130 along the horizontal meridian. The stimuli are in place for 20 seconds. The instruction to user 122 before the task begins is to: "Quickly look back and forth between the two dots." During the task, the movement of one eye or both eyes of user 122 is tracked by the reflection of infrared LED light 134 into camera 136, and the data is stored on second computing device 146. In alternative embodiments, the data could be stored in memory disposed within visualization unit 124, and/or the data could be transmitted wirelessly and/or through a network to a remote database.

Next, a main sequence saccade task, which lasts about 90 seconds, is conducted on user 122. In this task, a white fixation circle on a black background appears at the beginning of every trial, either at the center of user screen 130 or at locations to the left of central fixation. After an unpredictable period of time of fixation, preferably about 0.5-1.5 seconds, the fixation circle jumps to the right, forcing the subject to make a saccade in order to follow the stimulus. The instruction provided to user 122 is: "Follow the jumping dot." There are 6 different target displacements per block and subjects repeat the blocks 10 times for a total of 60 trials.

Next a smooth pursuit task, which lasts about 160 seconds, is conducted on user 122. In the smooth pursuit task, there are 1-dimensional and 2-dimensional sinusoidally moving stimuli. The instruction provided to user 122 is: "Follow the moving dot." The three 1-dimensional stimuli are horizontally moving, white dots, preferably moving at 0.50, 1.0, or 1.25 Hz on a black background. The two 2-dimensional stimuli are fractional sine and cosine functions (for example y=sin(2/3*f) and x=cos(5/7*f)) resulting in stimuli that constantly change direction in an unpredictable fashion. However, when the individual vertical and horizontal components of stimulus and eye motion are plotted, the simple sine and cosine functions are revealed, allowing for sophisticated analyses based on how accurately the eye or eyes of user 122 has tracked the motion of the stimuli. (e.g., FIGS. 8-11). The 5 pursuit stimuli are shown for 8 seconds and each are repeated 4 times.

After the smooth pursuit task, an optokinetic task, which lasts about 90 seconds, is conducted on user 122. In the optokinetic task, user 122 fixates on a white circle for preferably between about 0.5-1.5 seconds on a 50% grey background. Then the fixation point is extinguished, and a field of dynamically moving dots, masked by noise, drift left or right for 1 second. Fifty percent of the dots are white and 50% are black, thus the net illumination of user screen 130 is approximately 50% grey. The dots always move with motion coherence of 0.90 (see, e.g., Newsome and Pare, J. Neuroscience 1988). The instructions to the subject are "Fixate on the dot."

Next, the self-paced saccade task is repeated by user 122. After the 5 tasks, the experiment is complete. Throughout the entire experiment, user 122 stands on balance board 140, optionally a Wii Balance Board, and the motion and stance of user 122 are measured and recorded throughout all of the tasks performed. Balance board 140 can measure and record movements such as left/right movement, forward/rearward movement, sway, and stability. In some embodiments, in addition to the tasks described above, "natural viewing" tasks could be executed for user 122. For example, user 122 could be shown natural scenes, photographs, a scene from a television show(s), a scene from a movie(s), and/or any similar image. Visualization unit 124 could then be used to measure and track the eye movement of user 122 while watching the natural viewing task. Then, this natural viewing eye movement data of user 122 after a potential mTBI could be compared to the data from one or more baseline tests of user 122 and/or other non-concussed subjects to diagnose an mTBI.

After an mTBI, by simultaneously measuring and tracking both eye movements and balance at the same time with exemplary systems of the present disclosure, there are more parameters being measured than in a standard test for mTBI. A user with an mTBI cannot easily focus on making his or her balance appear to be normal while also focusing on eye movement tasks provided by visualization unit 124.

In some embodiments, since oculomotor variables are generally skewed and non-Gaussian, a two-sample Kolmogorov-Smirnov test is used in testing to determine if a variable significantly changed from baseline. A Pearson's r correlation (with a Bonferroni correction for multiple-comparison) is used to determine whether there is a correlation between change-from-baseline on any oculomotor variable and change-from-baseline on any ImPACT™ test variable.

Additionally, a stepwise discriminant function analysis (DFA) can be performed to identify variables that discriminate between concussed and control athlete groups. In a preferred analysis, the test is conducted three times: one with change from baseline of oculomotor variables alone, once with change from baseline of the 10 ImPACT™ variables alone, and once with both sets of variables combined. The stepwise feature of this analysis identifies which variables are most important for classification between groups, with non-predictive variables dropping out.

In the example provided above, between four and 10 variables are recorded during each eye movement task, all of which are continuously measured and recorded by second computing device 146. These variables are shown in Table 1 herein. A continuous measure of balance of user 122 is also collected from balance board 140. For each variable collected, the change of the variable for user 122 when healthy and non-concussed is calculated between at least two baseline tests (thus measuring test-retest variability). Then, when user 122 is suspected to have suffered an mTBI, the change between the measured baseline test variables and the measured variables after a suspected mTBI are calculated.

To validate such a system on a large scale, the change scores for healthy subjects in comparison to concussed subjects are provided to a multivariate classifier (for example, Linear Discriminant Analysis and/or a Support Vector Machine). Once the classifiers have been trained, subsequent users can be categorized as healthy or concussed by the operator.

In addition to the steps described above, motion correction can be executed on the raw video stream that is recorded before any subsequent analysis. For example, if user 122 moves during the tasks, immediately following the eye movement recording, motion correction algorithms are performed before any subsequent analyses on the recorded variables. In some embodiments, the example provided above is carried out on a portable, relatively small, completely battery powered, and rapid set-up system. Such a system can be used in direct sunlight, making visualization unit 124 feasible for use on the sidelines of any concussion-prone sport, and convenient for tracking recovery during medical follow-ups.

Figure 8:
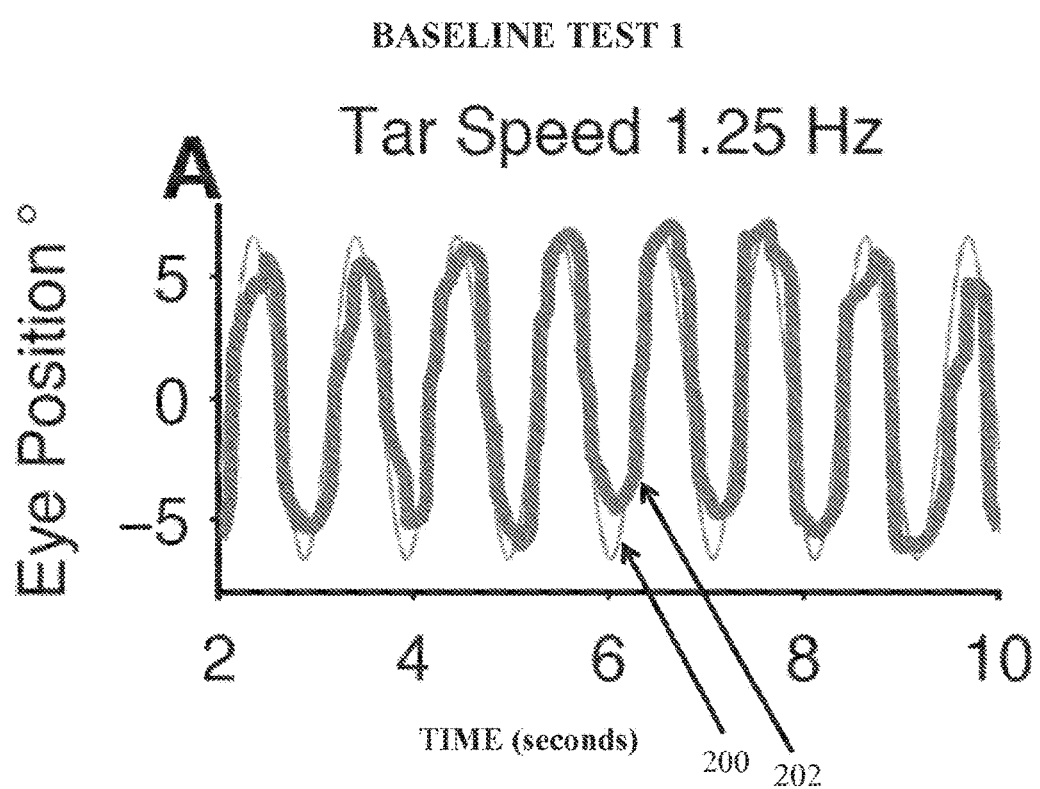
FIGS. 8-9 are graphical representations of data collected during a smooth pursuit task at baseline.

Referring now to FIGS. 8-13, example data collected from the experiment as described above is provided in graphical form. FIG. 8 provides a graphical representation of data collected during a smooth pursuit task as described above. The data in FIG. 8 is collected at a target speed of 1.25 Hz during a user's first baseline test. The Y-axis shows the user's eye position in degrees, and this is plotted against time in seconds.

In the smooth pursuit task, there are 1-dimensional and 2-dimensional sinusoidally moving stimuli. This is represented in FIG. 8 by target data 200. The instruction provided to a user is: "Follow the moving dot." The three 1-dimensional stimuli are horizontally moving, white dots, preferably moving at 0.50, 1.0, or 1.25 Hz on a black background. The two 2-dimensional stimuli are fractional sine and cosine functions (for example $y=\sin(2/3*f)$ and $x=\cos(5/7*f)$) resulting in stimuli that constantly change direction in an unpredictable fashion. However, when the individual vertical and horizontal components of stimulus and eye motion are plotted, the simple sine and cosine functions are revealed, allowing for sophisticated analyses based on how accurately the eye or eyes of user 122 has tracked the motion of the stimuli. The 5 pursuit stimuli are shown for 8 seconds and each are repeated 4 times. Eye movement data 202 represents how closely the eye or eyes of user 122 tracked the stimuli. Pursuit eye movement gain is calculated as eye speed divided by stimulus speed for every data point.

Figure 9:
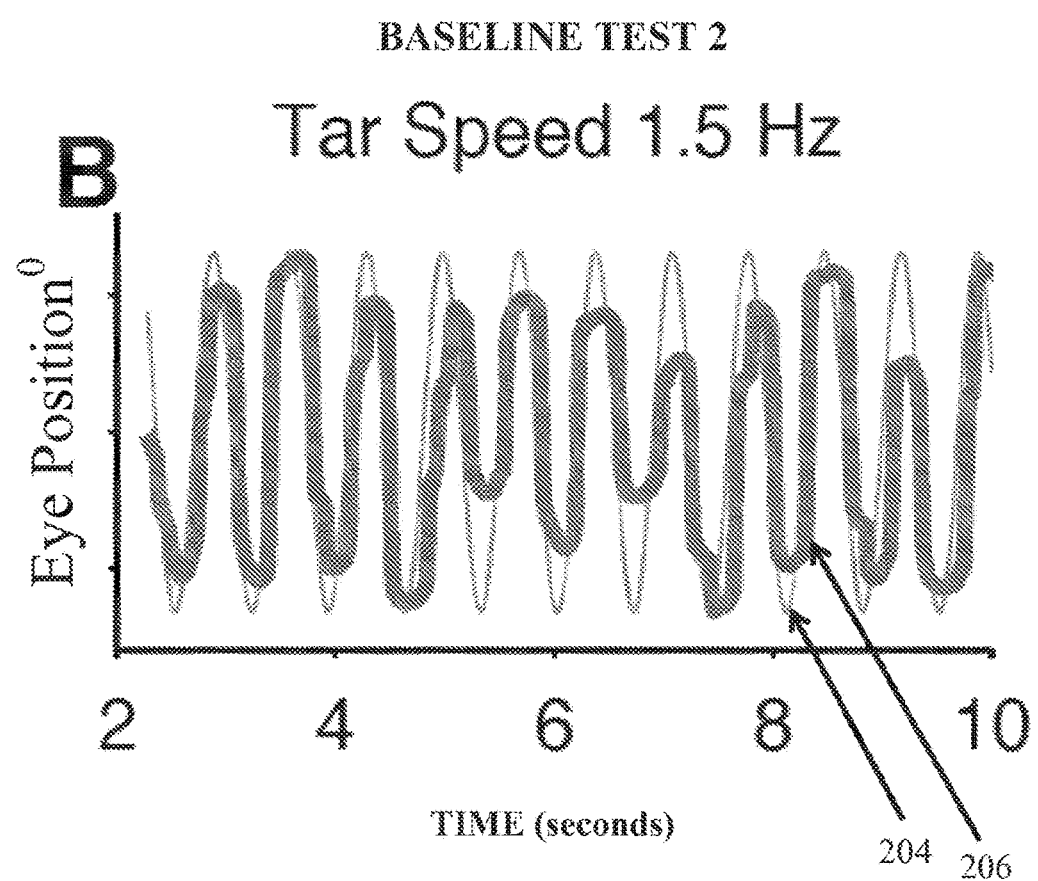

FIG. 9 also provides a graphical representation of data collected during a smooth pursuit task as described above. The data in FIG. 9 is collected at a target speed of 1.5 Hz during a user's second baseline test. The Y-axis shows the user's eye position in degrees, and this is plotted against time in seconds. In the smooth pursuit task, there are 1-dimensional and 2-dimensional sinusoidally moving stimuli. This is represented in FIG. 9 by target data 204. Eye movement data 206 represents how closely the eye or eyes of a user tracked the stimuli. Pursuit eye movement gain is calculated as eye speed divided by stimulus speed for every data point.

Figure 10:
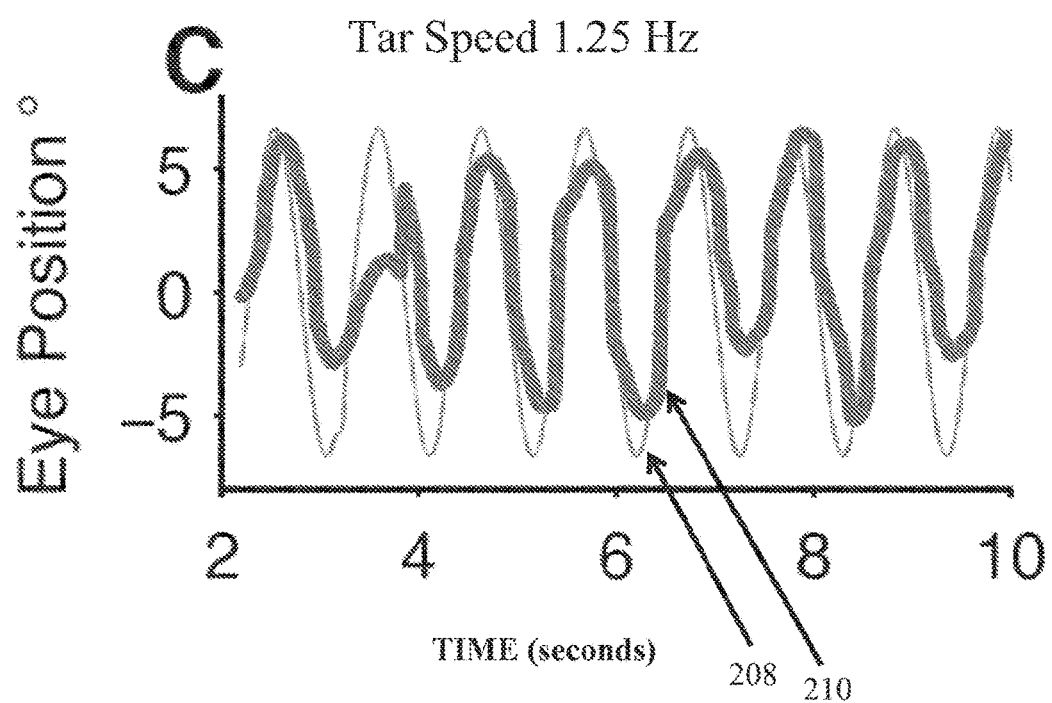
FIGS. 10-11 are graphical representations of data collected during a smooth pursuit task post-concussion.

FIG. 10 provides a graphical representation of data collected during a smooth pursuit task as described above. The data in FIG. 10 is collected at a target speed of 1.25 Hz during a first post-concussion test of user 122. The Y-axis shows the user's eye position in degrees, and this is plotted against time in seconds. In the smooth pursuit task, there are 1-dimensional and 2-dimensional sinusoidally moving stimuli. This is represented in FIG. 10 by target data 208. Eye movement data 210 represents how closely the eye or eyes of a user tracked the stimuli. Pursuit eye movement gain is calculated as eye speed divided by stimulus speed for every data point. As shown in FIG. 10 vs. the data shown in FIG. 8, the user's eye or eyes have not followed the stimuli as closely during the post-concussion test as during the baseline test.

Figure 11:
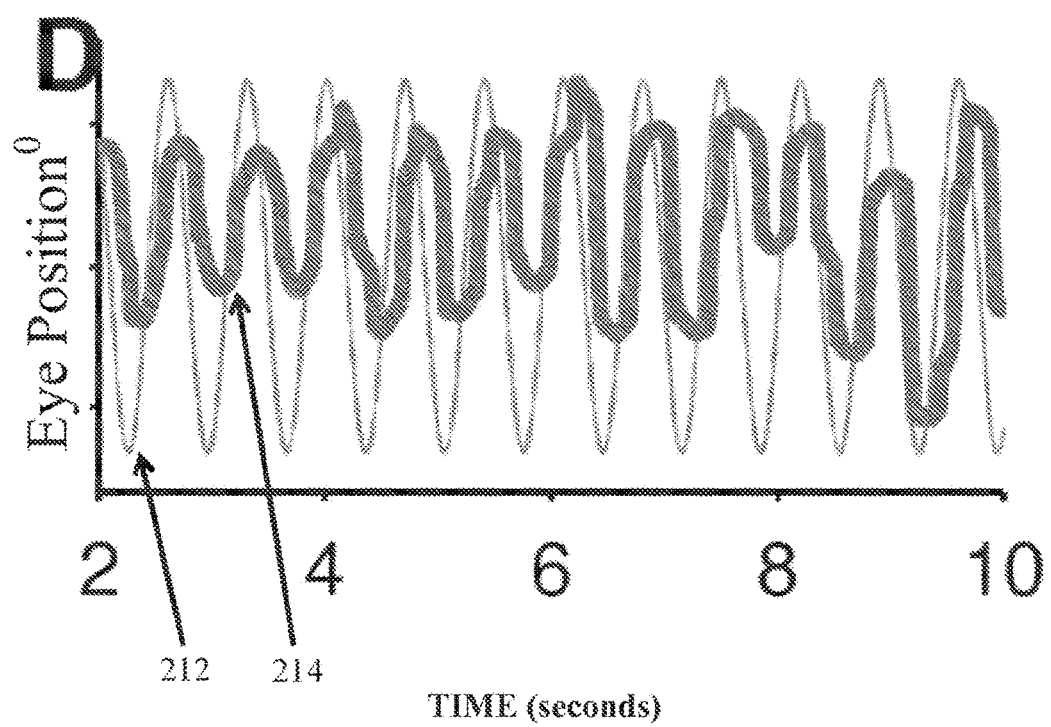

FIG. 11 provides a graphical representation of data collected during a smooth pursuit task as described above. The data in FIG. 11 is collected at a target speed of 1.5 Hz during a user's second post-concussion test. The Y-axis shows the user's eye position in degrees, and this is plotted against time in seconds. In the smooth pursuit task, there are 1-dimensional and 2-dimensional sinusoidally moving stimuli. This is represented in FIG. 11 by target data 212. Eye movement data 214 represents how closely the eye or eyes of a user tracked the stimuli. Pursuit eye movement gain is calculated as eye speed divided by stimulus speed for every data point. As shown in FIG. 11 vs. the data shown in FIG. 9, the user's eye or eyes have not followed the stimuli as closely during the post-concussion test as during the baseline test.

Figure 12:
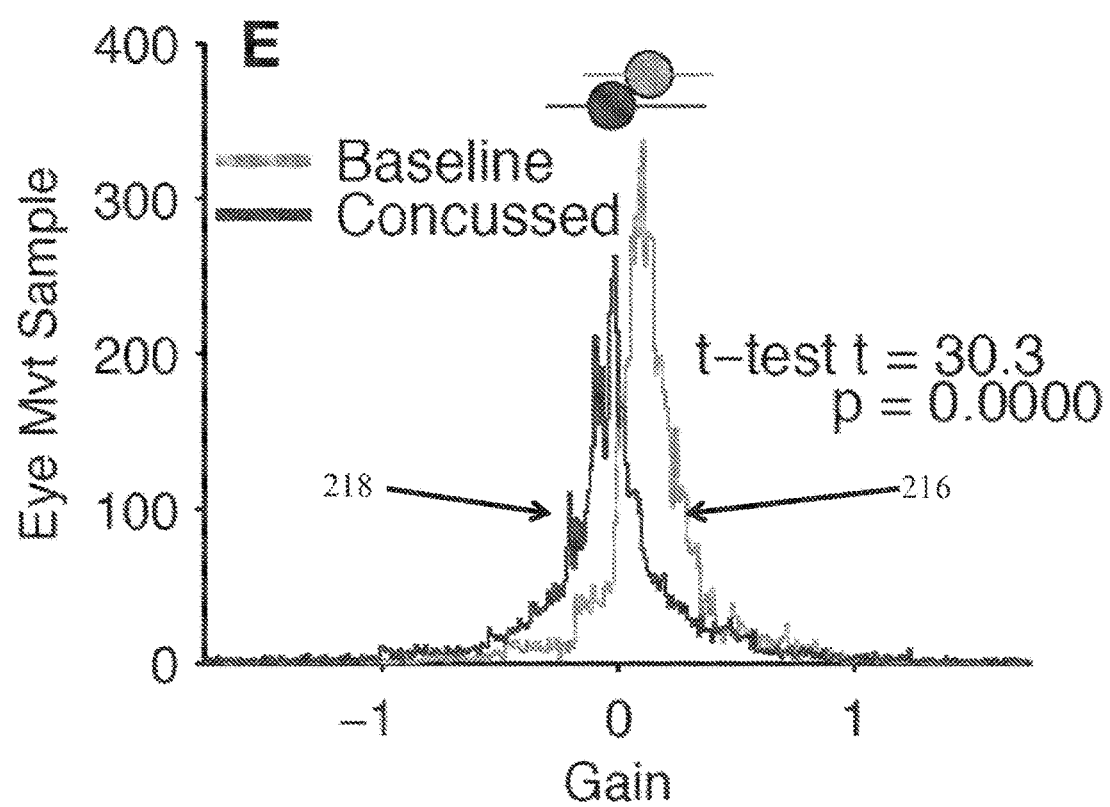
FIG. 12 is a graphical representation of smooth pursuit gain responses of a population for the baseline trials of FIGS. 8-9 and post-concussion testing of FIGS. 10-11.

FIG. 12 shows the baseline population smooth pursuit gain response 216 for the trials of FIGS. 8-9, and post-concussion smooth pursuit gain response 218 of FIGS. 10-11 for the example provided above for one user or subject (i.e., a "within subjects analysis"). As noted, pursuit eye movement gain is calculated as eye speed divided by stimulus speed for every data point. As can be seen, the gain calculated for the data points recorded when a user is concussed causes the graph to shift away from the gain calculated for the data points recorded during a user's baseline test(s).

Figure 13:
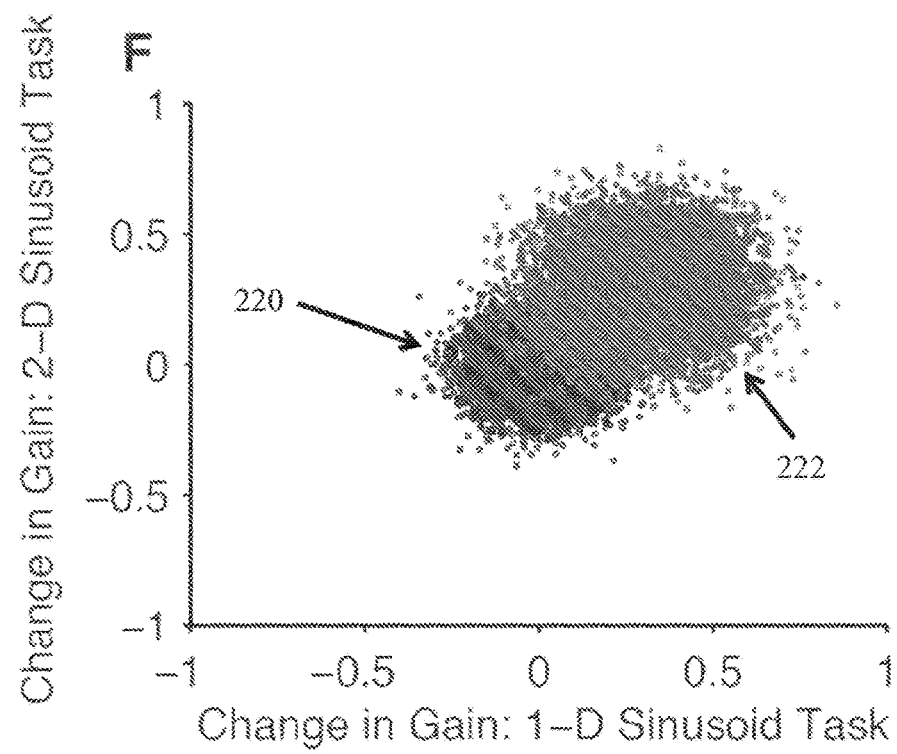
FIG. 13 is a graphical representation of the change in gain for two subjects in two tasks, a 1-D sinusoid and a 2-D sinusoid.

FIG. 13 shows the change in gain for two subjects in two tasks (1-D sinusoid and 2-D sinusoid) (i.e. a "between subjects analysis"). The cloud of data points 220 disposed in the lower-left portion of the graph shows changes in gain for a healthy, matched subject between two eye movement recordings. The cloud of data points 222 disposed in the upper-right portion of the graph shows changes in gain for a concussed athlete in two pursuit tasks. FIG. 13 shows a larger change in gain for the concussed subject between baseline and post-injury tests versus the change in gain for the non-concussed subject between baseline tests.

The data recorded and collected with the tasks of the present disclosure can be analyzed by a pattern classifier in multi-dimensional space. For example, single-subject or single-user data could be combined with the results of every concussed and nonconcussed athlete previously tested (between subjects analysis) on every task (22 dimensions, for example the 22 dimensions of Table 1) to create a cloud of data. A random sample of 75% of the pairs is used, in some embodiments, in order to train the analytic classifier of mTBI and to test its accuracy on the remaining 25% of the sample. Such random sampling and classification may be redone approximately 10,000 times, selecting a different 75% random sample each time. The classifier then determines which data combination provides the highest sensitivity and specificity in predicting concussion.

Figure 14:
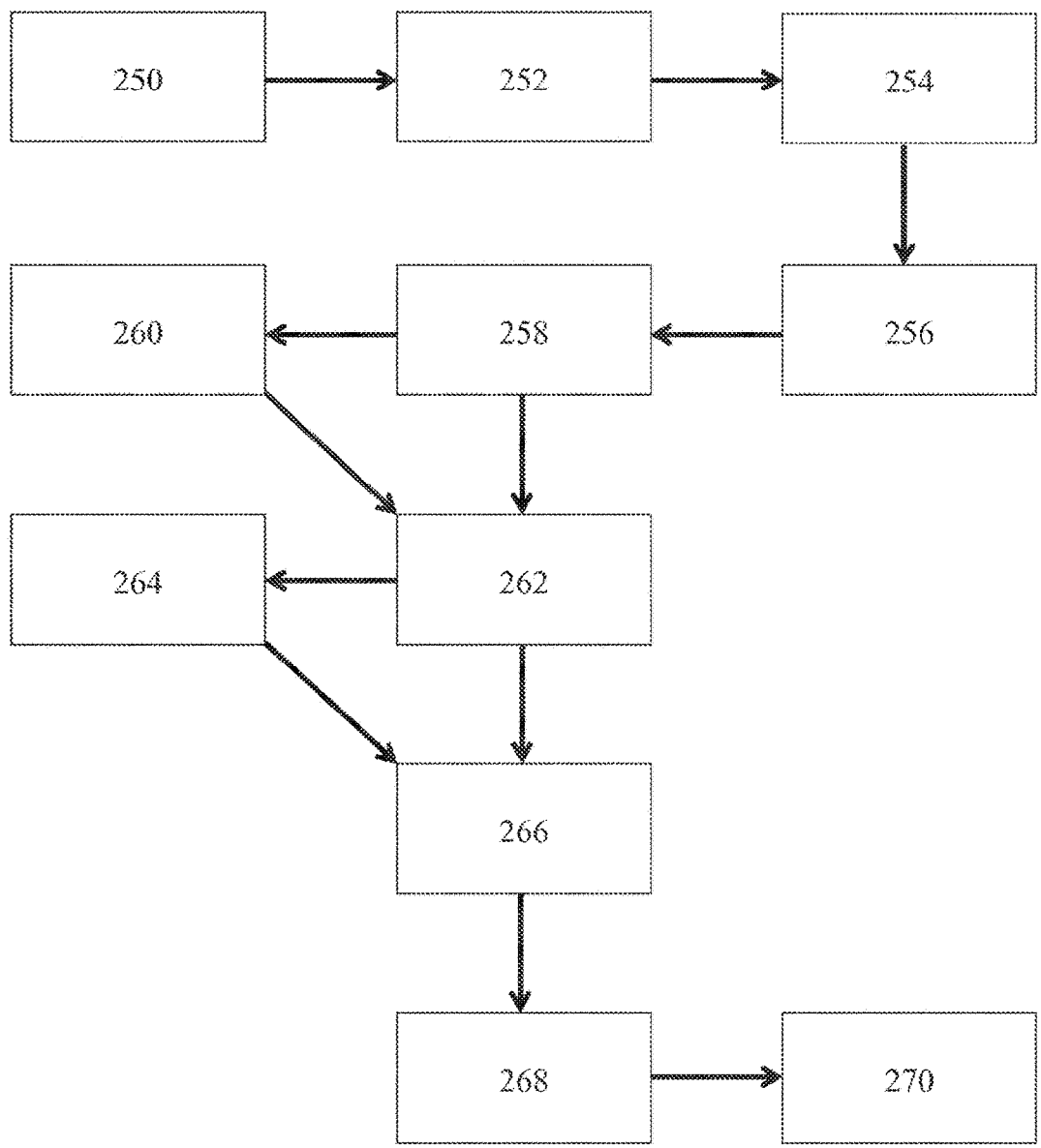
FIG. 14 is a flowchart depicting a diagram of the steps of one embodiment of a system for detection of an mTBI.

Referring now to FIG. 14, a diagram of the steps of one embodiment of a system for detection of mTBI is shown. At step 250, one or more users are given a baseline test to measure and record one or more eye movement variables specific to the user. The users, in some embodiments, are athletes on a sports team, but in other embodiments may be persons in a line of work with a high risk of mTBI. The eye movement variables measured and recorded might include those variables shown above in Table 1, or the combination of variables provided in the example above. At step 252, each user is given a second baseline test at some later time, optionally days or months after the first baseline test, to account for an individual user's test-retest variability.

At step 254, a user encounters a possible mTBI, such as a possible concussion. Such an event may occur in a sports game or in a user's line of work. At step 256, an mTBI detection system, such as for example system 120 of FIG. 2, is provided and set up at the user's location for mTBI testing. At step 258, the mTBI detection system is calibrated to the user, for example as described above using a 13-point calibration task. Step 260 is an optional calibration validation task, such as for example the 13-point calibration task described in the example above.

At step 262, the user is given a series of tasks, which can be any combination of the tasks described herein, and the eye movement data and stimuli data are tracked and recorded by a computing device. If a balance detecting device is used, this data is also tracked and recorded during the eye movement tasks. At step 266, the user's test data is compared to the user's baseline data to determine if it is likely that the user has suffered a concussion.

The data recorded and collected with the tasks of the present disclosure in step 262 can be analyzed by a pattern classifier in multi-dimensional space at optional step 264. For example, single-subject or single-user data collected at step 262 would be combined with the results of every concussed and nonconcussed athlete previously tested (between subjects analysis) on every task (22 or more dimensions, for example the 22 dimensions of Table 1) to create a cloud of data at step 264. A random sample of 75% of the pairs is used, in some embodiments, in order to train the analytic classifier and to test its accuracy on the remaining 25% of the sample. Such random sampling and classification may be redone approximately 10,000 times, selecting a different 75% random sample each time. The classifier then determines which data combination provides the highest sensitivity and specificity in predicting concussion at step 266.

Using Support-Vector Machines and/or Linear Discriminant Analysis look at the pattern of changes in multi-dimensional space (e.g. 22+ dimensions) across your whole training data. Since every injury and the cognitive reserve of every person is different, the behavioral deficits will be different in every patient. Multi-dimensional analysis is much more powerful than what they are doing.

At step 268, the user can be retested at one time or multiple times after step 266, if it is determined at step 266 that the user has an mTBI, such as a concussion. Retesting could be done days and/or months after an mTBI is detected. At step 270, a user's eye movement scores on the tasks after an mTBI could be compared to the user's baseline, and if the scores were comparable or close to the baseline scores, then a doctor or similarly qualified individual could make a "return to play" or "return to work" decision for the user.

Thus, the present disclosure provides a device to detect mild traumatic brain injury with user eye movement, comprising a mobile, wearable, and high spatial-temporal resolution eye tracking device.

Additionally, a method of detecting mild traumatic brain injury is disclosed comprising: (1) a user wearing a headset which tracks and records the user's eye movement data; (2) comparing the user's eye movement data to standard eye movement data for a person not suffering from mild traumatic brain injury; and (3) determining whether the user has suffered a mild traumatic brain injury by analyzing the difference between the user's recorded eye movement data and the eye movement data for a person not suffering from mild traumatic brain injury.

The embodiments disclosed herein are not intended to be exhaustive or limit the disclosure to the precise form disclosed in the preceding detailed description. Rather, the embodiments are chosen and described so that others skilled in the art may utilize their teachings.

What is claimed is:

1. A device to detect mild traumatic brain injury ("mTBI") by user eye movement comprising:
   a portable visualization unit comprising a light and a camera, wherein the visualization unit is configured to reflect light off of a user's eye into the camera;
   a user screen viewable by the user and configured to display a series of tasks to the user which require movement of the user's eye, such movements being tracked by the visualization unit, the series of tasks including at least one of a sinusoidal pursuit task, a step-ramp pursuit task, and a 2-dimensional unpredictable pursuit task, to measure at least one of pursuit gain and pursuit lag; and
   a first computing device in communication with the visualization unit, wherein the first computing device receives eye movement data including at least 22 variables from the visualization unit in response to the user performing the series of tasks, the first computing device being configured to calculate a difference between at least one measured variable of the eye movement data when the user is unimpaired and the at least one measured variable after the user experiences a potential mTBI.

2. The device according to claim 1, wherein the device is portable and wearable by the user.

3. The device according to claim 1, wherein the series of tasks is executed in less than eight minutes.

4. The device according to claim 1, further comprising a device configured to measure the user's balance during the series of tasks.

5. The device according to claim 4, wherein the device is a balance detecting device coupled to the first computing device configured to measure the user's balance by sensing pressure applied at different points of feet of the user.

6. The device according to claim 1, further comprising a second computing device and an operator's screen for operation of the visualization unit.

7. The device according to claim 6, wherein the user screen and operator screen provide either an indication of likely concussed or likely not concussed based on the difference between the values of at least one measured variable.

8. The device according to claim 1, wherein the visualization unit further comprises user controls and an audio unit.

9. The device according to claim 1, wherein the user's unimpaired baseline score for the at least one variable is an average of two baseline task scores for the user taken at two different times when the user is unimpaired.

10. A method of detecting mild traumatic brain injury ("mTBI") comprising:
    providing a visualization unit for a user suspected of suffering an mTBI which can track the user's eye movement and record resulting eye movement data including at least 22 variables by a camera and a first computing device;
    presenting to the user a series of tasks designed to require the user to move the user's eyes pursuant to specified directions, the series of tasks including a self-paced saccade task;

measuring, in response to the user performing the series of tasks, corrective saccades;

recording the user's eye movement data in response to the user performing the series of tasks; and determining whether the user has suffered an mTBI by analyzing a difference between the user's recorded eye movement data and the eye movement data for a person not suffering from mTBI.

11. The method according to claim 10, wherein the visualization unit is portable and wearable by the user.

12. The method according to claim 10, wherein the series of tasks further include at least one of a self-paced saccade task, a sinusoidal pursuit task, a step-ramp pursuit task, an ocular following task, and a dynamic random dot task, and wherein the series of tasks is executed in less than eight minutes.

13. The method according to claim 10, further comprising the step of providing a device configured to measure the user's balance during the series of tasks.

14. The method according to claim 10, wherein the step of executing further comprises a second computing device and an operator's screen for operation of the visualization unit.

15. The method according to claim 10, wherein the visualization unit further comprises user controls and an audio unit.

16. The method according to claim 10, further including the step of providing a visualization unit for a user not suspected of suffering an mTBI which can track and record the user's eye movement data by a camera and a first computing device, wherein the user's eye movement data provides the user's unimpaired baseline score for the at least one variable.

17. The method according to claim 10, further comprising providing an indication of likely concussed or likely not concussed based on the difference between the user's recorded eye movement data and the eye movement data for a person not suffering from mTBI.

18. The method of claim 10, wherein determining whether the user has suffered an mTBI comprises training a multivariate classifier and categorizing the user as healthy or concussed by providing the user's recorded eye movement data to the multivariate classifier.

19. The method of claim 10, further comprising using a motion correction algorithm immediately after recording the user's eye movement data to correct for movement of the user during the series of tasks.

20. The method of claim 10, wherein measuring further comprises measuring saccadic velocity, saccadic amplitude, saccade response time, and saccadic drift.

21. A system to detect mild traumatic brain injury ("mTBI") by user eye movement comprising:

a visualization unit comprising a light and a camera, wherein the visualization unit is configured to reflect light off of a user's eye into the camera;

a user screen, wherein the screen is viewable by the user and wherein the screen is configured to display a series of tasks to the user to measure the user's eye movement by the camera;

a device for measuring the user's balance during the series of tasks;

a first computing device in communication with the visualization unit, wherein the first computing device receives eye movement data including at least 22 variables from the visualization unit in response to the user performing the series of tasks, the first computing device being configured to calculate a difference between at least one measured variable of the eye movement data when the user is unimpaired and the at least one measured variable after the user experiences a potential mTBI; and software-implemented logic to determine if the difference between the at least one measured variable of the eye movement data when the user is unimpaired and the at least one measured variable after the user experiences a potential mTBI is great enough to indicate a likelihood of an mTBI.

22. The system according to claim 21, wherein the series of tasks further include at least one of a self-paced saccade task, a sinusoidal pursuit task, a step-ramp pursuit task, an ocular following task, and a dynamic random dot task, and wherein the series of tasks is executed in less than eight minutes.

23. The system according to claim 21, further comprising a second computing device and an operator's screen for operation of the visualization unit.

24. The system according to claim 21, wherein the visualization unit further comprises user controls and an audio unit.

25. The system according to claim 21, wherein the the at least one measured variable of the eye movement data when the user is unimpaired is an average of two baseline task scores for the user taken at times when the user is unimpaired.

26. The system according to claim 23, wherein the user screen and operator screen provide either an indication of likely concussed or likely not concussed based on the difference between the values of the at least one measured variable.

27. The system of claim 21, wherein the visualization unit is configured to track a location of a pupil of the user and a corneal reflection of the light in real time.

28. The system of claim 27, further including an operator screen that displays the pupil and the corneal reflection in false color to an operator in real time.

29. The system of claim 28, wherein the operator screen displays cross hairs on both the false color pupil and the false color corneal reflection.

30. The system of claim 29, wherein the operator screen further displays a first locator indicating a real time location of a stimuli being viewed by the user on the user's screen and a second locator indicating a location of where the eye of the user is presently looking.

31. The system of claim 30, wherein the operator screen further displays a third locator indicating a location of where the eye of the user is presently looking corrected for eye drift.

* * * * *